United States Patent [19]

Traxler

[11] 4,251,517

[45] Feb. 17, 1981

[54] UNSATURATED OR SUBSTITUTED METHYL ETHERS HAVING ANTIBIOTIC ACTIVITY

[75] Inventor: Peter Traxler, Allschwil, Switzerland

[73] Assignee: Ciba-Geigy Corporation, Ardsley, N.Y.

[21] Appl. No.: 52,362

[22] Filed: Jun. 27, 1979

Related U.S. Application Data

[63] Continuation of Ser. No. 830,503, Sep. 6, 1977, abandoned.

[30] Foreign Application Priority Data

Sep. 9, 1976 [LU] Luxembourg .......................... 75760

[51] Int. Cl.³ ...................... A61K 31/71; C07H 13/12
[52] U.S. Cl. ..................................... 424/180; 424/181; 435/100; 536/4; 536/17 R; 536/119; 536/120
[58] Field of Search ........................... 536/4, 120, 119; 424/180

[56] References Cited

U.S. PATENT DOCUMENTS

| | | | |
|---|---|---|---|
| 2,218,569 | 10/1940 | White | 536/4 |
| 2,235,785 | 3/1941 | White | 536/4 |
| 2,235,786 | 3/1941 | White | 536/4 |
| 2,258,171 | 10/1941 | Barry | 536/120 |
| 3,408,441 | 10/1968 | von Wartburg et al. | 536/4 |
| 3,781,267 | 12/1973 | Jaques et al. | 536/4 |
| 3,935,184 | 1/1976 | Jones et al. | 536/4 |
| 4,017,608 | 4/1977 | Gordon | 536/4 |

*Primary Examiner*—Johnnie R. Brown
*Attorney, Agent, or Firm*—Prabodh I. Almaula

[57] ABSTRACT

The antibiotics Papulacandin A and Papulacandin B are etherified at the phenolic groups in positions 10 and/or 12 by introducing a group

—CH$_2$—K wherein K is a hydrocarbon radical which is either unsaturated and aliphatic, or it is saturated or unsaturated and substituted by cyclic hydrocarbons, such as aromatic or heterocyclic ones, or by functional groups, such as halogens, carboxyl groups, carboxyl ester or amide groups. These ethers are characterized by a good antifungal action e.g. against *Candida albicans* and also by an antifiral action.

13 Claims, 2 Drawing Figures

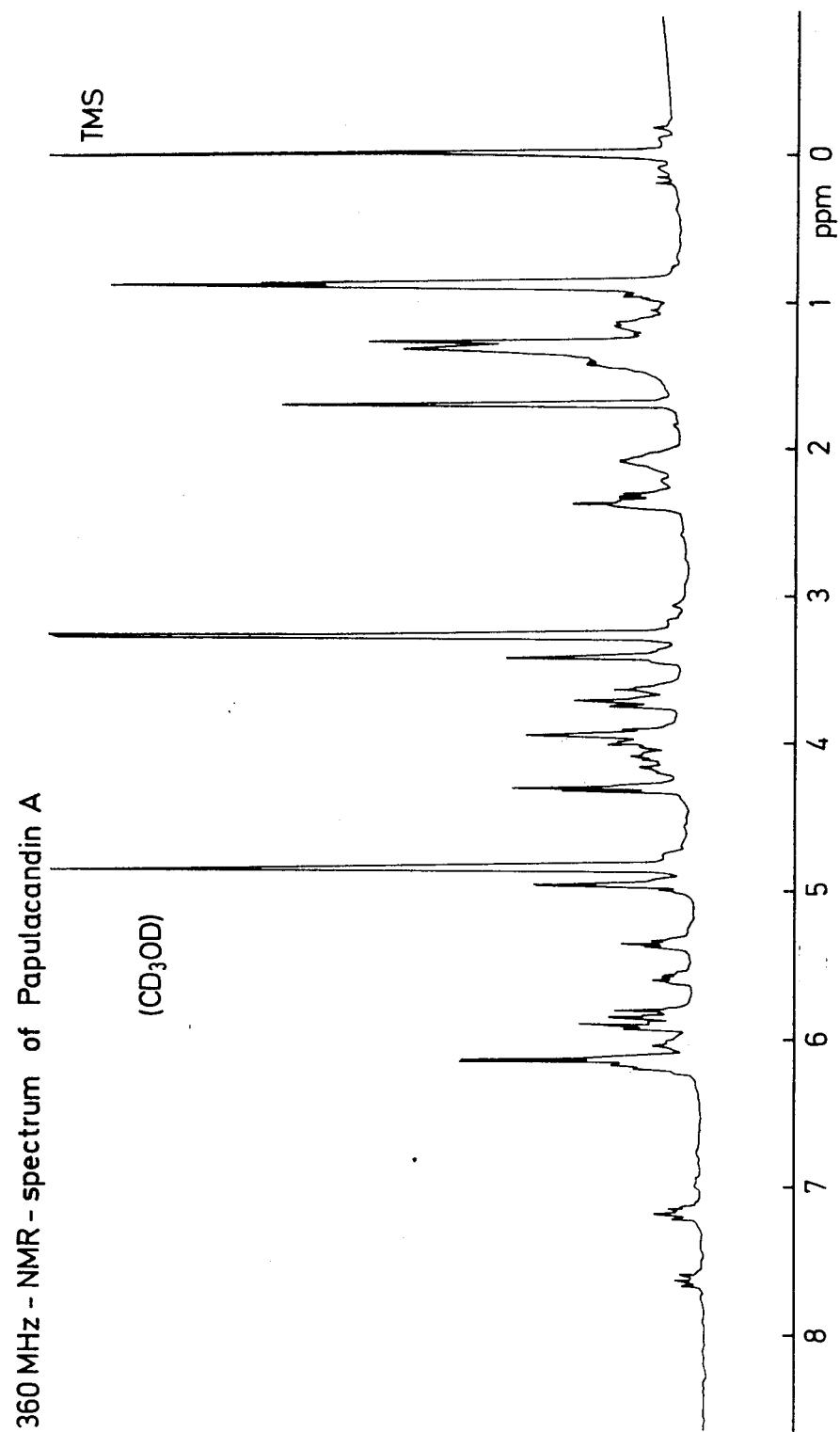
Fig.1 360 MHz-NMR-spectrum of Papulacandin A (CD₃OD)

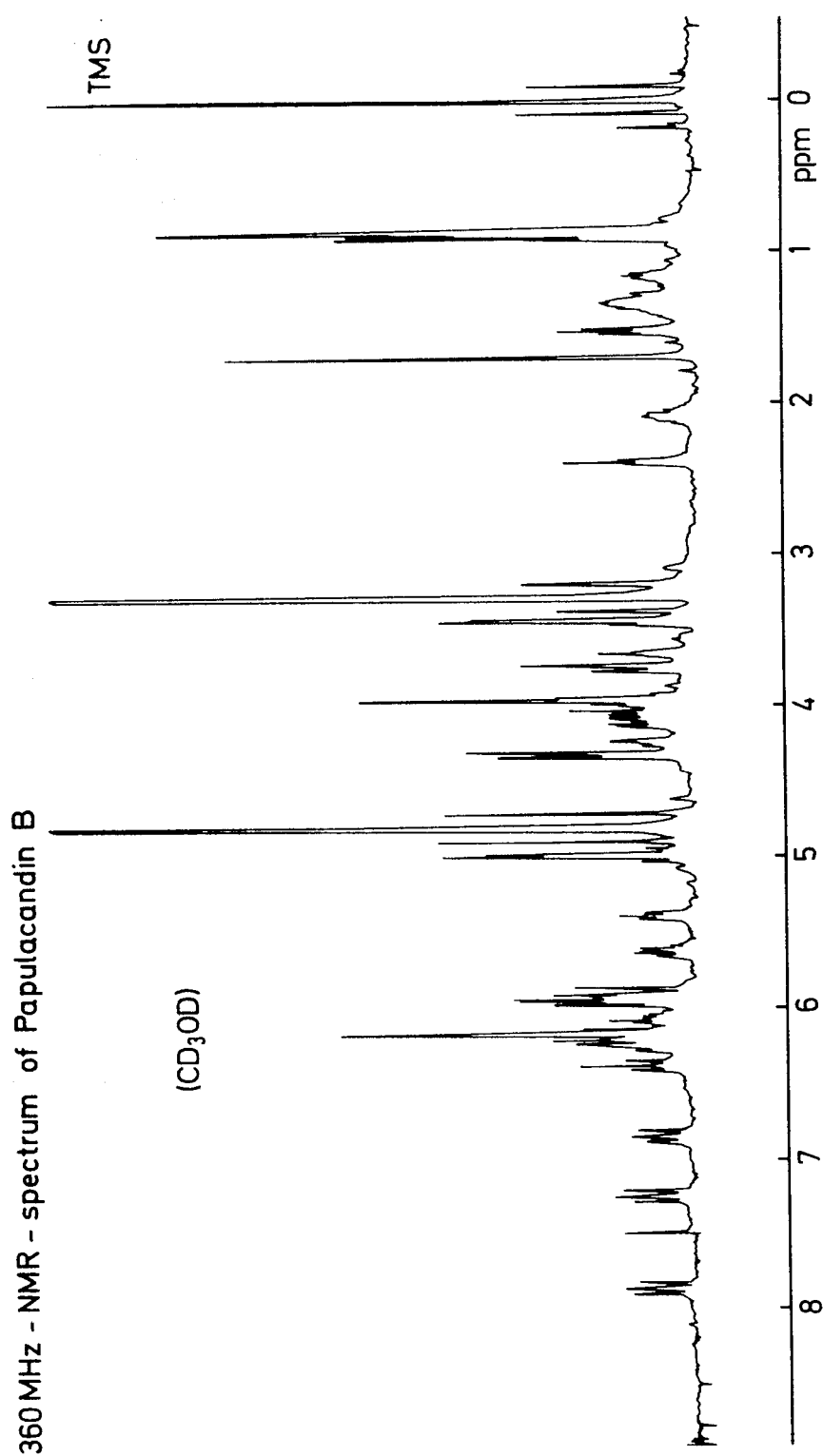

UNSATURATED OR SUBSTITUTED METHYL ETHERS HAVING ANTIBIOTIC ACTIVITY

This is a continuation of application Ser. No. 830,503 filed on Sept. 6, 1977, now abandoned.

The present invention relates to Papulacandin derivatives and in particular to a group of ethers of Papulacandin A and B which are of interest on account of their good antibiotic action against fungi and also because they are useful intermediates for the production of other compounds having antibiotic action.

The new antibiotic "A 32283" has been described in German Offenlegungsschrift No. 2,609,611. It is obtained by culturing a specific strain of the species *Papularia sphaerosperma* (Pers.) Höhnel, (strain A 322883), deposited in the Nothern Regional Research Lab., U.S. Department of Agriculture, Peoria, Illinois, under the number NRRL 8086. As disclosed in the German Offenlegungsschrift referred to above, the antibiotic obtained by culturing this micro-organism—to which the name "Papalucandin" has been given—consists in the main of two components having antibiotic action, namely 70% of a component B (Papulacandin B) and 20% of a component A (Papalucandin A), whilst the remainder (approx. 10%) consists of a number of subsidiary components which have been designated as components C, D and E (Papulacandin C, D and E). At the present time, the ultimate constitution of Papulacandin A and B has been clarified. Accordingly, Papulacandin B has the formula

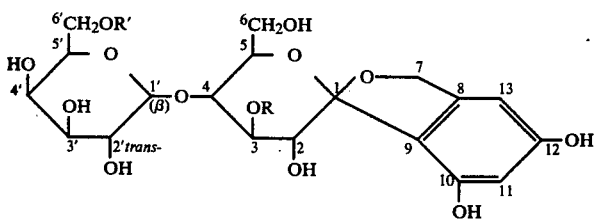

wherein

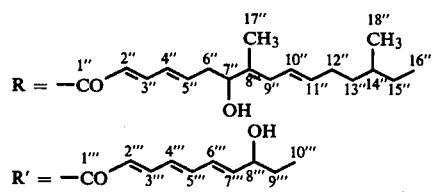

and Papalucandin A has the formula

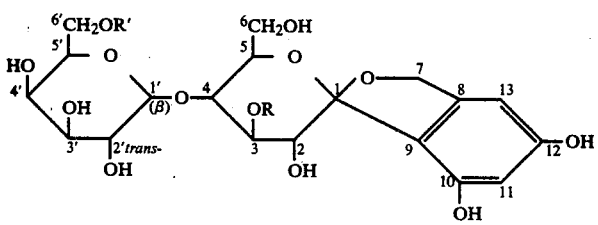

wherein

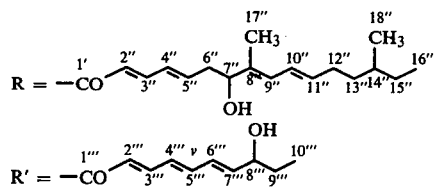

In the German Offenlegungsschrift referred to above, functional derivatives of Papulacandin A and B are also described, in particular esters in which the alcoholic hydroxyl groups are esterified with carboxylic acids or thiocarboxylic acids, and ethers in which the phenolic hydroxyl groups are etherified with alcohols, in particular with lower alkanols, especially methanol, whilst one or both phenolic hydroxyl groups can be etherified. Like the base substances themselves, Papulacandin A and B, all these derivatives have an antifungal action against Hyphomycetes and against yeast-like fungi, in particular *Candida albicans*.

The present invention relates to a special group of mono- and diethers of Papulacandin A and B, namely those having the partial formula

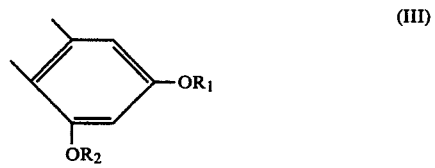 (III)

(I)

(II)

of the aromatic ring in Papulacandin A or B, wherein each of $R_1$ and $R_2$ represents hydrogen or a hydrocarbon radical of the formula $$-CH_2-K \qquad (IV)$$

wherein K represents an unsaturated aliphatic hydrocarbon radical, a carbocyclic hydrocarbon radical or a heterocyclic radical, or represents an aliphatic hydrocarbon radical which is saturated or unsaturated in the aliphatic part and is substituted by a mono- or divalent carbocyclic hydrocarbon radical or heterocyclic radical, or represents one of these radicals which is substituted in any position by functional groups, or represents a saturated aliphatic hydrocarbon radical which is substituted in any position by functional groups, with the proviso that at least one of the symbols $R_1$ and $R_2$ represents the hydrocarbon radical of the formula (IV).

The hydrocarbon radical of the formula (IV) preferably contains not more than 24 carbon atoms, and in particular contains from 1 to 12 carbon atoms.

An unsaturated aliphatic hydrocarbon radical represented by K contains preferably from 1 to 7 carbon atoms and is in particular an alkenyl or alkynyl radical, for example vinyl, allyl, propenyl, isopropenyl, 2- or 3-methallyl and 2- or 3-butenyl, propargyl or 2-butynyl. However, a number of ethylene and/or acetylene compounds can also be present.

The unsaturated aliphatic hydrocarbon radical which is substituted by cyclic hydrocarbon radicals and/or by functional groups also preferably contains from 1 to 7 carbon atoms and is, for example, one of the specific radicals mentioned above which contains the cited substituents. A corresponding saturated aliphatic hydrocarbon radical is for example an alkyl radical of 1 to 7 carbon atoms, such as methyl, ethyl, propyl, isopropyl, n-butyl, isobutyl, tert-butyl, amyl, isoamyl, in which both the cited substituting cyclic radicals and/or the functional groups are at one or more of the carbon atoms, in particular also at the terminal carbon atoms of the alkyl radical.

A carbocyclic hydrocarbon radical can be a mono- or polycyclic aromatic hydrocarbon radical or an alicyclic hydrocarbon radical, whilst polycyclic radicals can also have mixed aromatic-alicyclic character. In particular, monocyclic radicals are possible, for example phenyl or phenylene for the aromatic radicals and cycloalkyl, cycloalkenyl or cycloalkadienyl for the alicyclic hydrocarbon radicals, chiefly those with 3- to 8-membered rings, but preferably with 5- or 6-membered rings, and their derivatives which are substituted by alkyl groups, in particular lower alkyl groups of 1 to 4 carbon atoms, especially methyl. Such monocyclic radicals are specifically exemplified by phenyl, o-, m- or p-tolyl, 2,3-xylyl or 3,5-xylyl, and corresponding divalent radicals, such as phenylene, 2,3-dimethylphenylene, 2,5-dimethylphenylene, 2,6-dimethylphenylene, cyclopropyl, cyclobutyl, cyclopentyl, cyclohexyl, cycloheptyl, or 1-, 2- or 3-cyclopentenyl and 1-, 2- or 3-cyclohexenyl, 1,4-cyclohexadienyl and corresponding divalent radicals, such as 1,4-cyclohexylene and the methylated derivatives thereof.

Heterocyclic radicals can have aromatic character or are corresponding partially or wholly saturated radicals. They can be mono- or polycyclic. Such radicals can be for example azacyclic, thiacyclic, oxacyclic, thiazacyclic, thiadiazacyclic, oxazacyclic, diazacyclic, triazacylic or tetraazacyclic radicals. Examples are: 2-pyrryl or 3-pyrryl, pyridyl, for example, 2-, 3- or 4-pyridyl and pyridinio, and thienyl, for example 2- or 3-thienyl, or furyl, for example 2-furyl; bicyclic monoaza-, monooxa- or monothiacyclic radicals, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl; monocyclic diaza-, triaza-, tetraaza, oxaaza-, thiaza- or thiadiazacyclic radicals, such as imidazolyl, for example 2-imidazolyl, pyrimidinyl, for example 2- or 4-pyrimidinyl, triazolyl, for example 1,2,4-triazol-3-yl, tetrazolyl, oxazolyl, isoxazolyl, thiazolyl, for example 2-thiazolyl, isothiazolyl, for example 3- or 4-isothiazolyl or 1,2,4- or 1,3,4-thiadiazolyl, for example 1,2,4-thiadiazol-3-yl or 1,3,4-thiadiazol-2-yl; or bicyclic diaza-, oxaza or thiazacyclic radicals, such as benzimidazolyl, for example 2-benzimidazolyl, benzoxazolyl, for example 2-benzoxazolyl, or benzthiazolyl, for example 2-benzthiazolyl. Corresponding partially or completely saturated radicals are for example tetrahydrothienyl, such as 2-tetrahydrothienyl, tetrahydrofuryl, such as 2-tetrahydrofuryl, pyrrolidyl, such as 2-pyrrolidyl, pyrrolidino and 2,3,4,5-tetramethylpyrrolidino, tetrahydropyridyl such as $\Delta^1$-, $\Delta^2$- or $\Delta^3$-piperideino or -piperideinyl, or piperidyl, such as piperidino, 2-, 3- or 4-piperidyl, and also morpholino, thiomorpholino, 1-piperazinyl and N'-lower alkylpiperazinyl, in particular N'-methylpiperazinyl. If the heterocyclic radical is not at the end of an aliphatic chain, then the radical is for example a divalent radical which corresponds to one of those mentioned above. These radicals can also be substituted, like the above mentioned carbocyclic groups, by lower alkyl groups of 1 to 4 carbon atoms, in particular by methyl groups.

The above described cyclic radicals can be bonded direct to the $CH_2$ group of the radical of the formula (IV), i.e. they represent K in that formula; but they can also occur as substituents of a saturated or unsaturated aliphatic hydrocarbon radical, namely terminally as monovalent radical or at another carbon atom of the aliphatic chain as divalent radical. The following partial formulae for the radicals $R_1$ and $R_2$ correspond to these cases:

$$R_1 \text{ or } R_2 = -CH_2-A_1 \qquad (V)$$

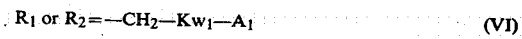

$$R_1 \text{ or } R_2 = -CH_2-Kw_1-A_1 \qquad (VI)$$

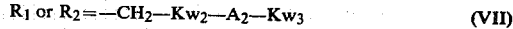

$$R_1 \text{ or } R_2 = -CH_2-Kw_2-A_2-Kw_3 \qquad (VII)$$

wherein $Kw_1$ represents a divalent saturated or unsaturated, linear or branched aliphatic hydrocarbon radical, preferably containing 1 to 17, in particular 1 to 7, carbon atoms, and each of $Kw_2$ and $Kw_3$ also represents such a radical, preferably in such a manner that $Kw_2$ and $Kw_3$ together do not contain more than 17, in particular not more than 7, carbon atoms, and $A_1$ represents a monovalent cyclic hydrocarbon radical, for example an aromatic, heterocyclic or alicyclic radical, in particular one of those mentioned above, and $A_2$ represents a corresponding divalent cyclic radical, for example one of those mentioned above.

Accordingly, the invention comprises ethers in accordance with the above general definition in which K represents a hydrocarbon radical which is substituted in any position by functional groups, i.e. by at least one or more identical or different groups of this kind. Possible functional groups are: free, etherified or esterified hydroxyl groups, mercapto, alkylthio, in particular lower alkylthio and substituted or unsubstituted phenylthio groups, halogen atoms, i.e. fluorine, chlorine, bromine or iodine atoms, cyano, azido, oxo and nitro groups, primary, secondary and tertiary amino groups and corresponding acylamino groups, as well as diacylamino groups, and sulphamino groups, caboxyl groups which can be functionally modified, carbamoyl, ureidocarbonyl or guanidinocarbonyl groups or sulpho groups whch can be functionally modified. These groups can be present as substituents both of the open hydrocarbon chains and of the ring systems.

An etherified hydroxyl group is for example a lower alkoxy group, such as the methoxy, ethoxy, propoxy, isopropoxy, butoxy and tert.-butoxy group, which can also be substituted. Thus such a lower alkoxy group can be substituted by halogen atoms, in particular in the 2-position, for example in the 2,2,2-trichloroethoxy, 2-chloroethoxy or 2-iodoethoxy moiety, or by lower alkoxy groups, especially in the 1-position, as in the butoxyethoxy moiety, or in the 2-position, as in the 2-methoxyethoxy moiety. In addition, etherified hydroxyl groups are also substituted or unsubstituted phenoxy and phenyl-lower alkoxy groups, in particular benzyloxy, benzhydryloxy and triphenylmethoxy (trityloxy) groups, and heterocyclyloxy groups, as in particular 2-tetrahydrofuranyloxy and 2-tetrahydropyranyloxy groups. Etherified hydroxyl groups are also to be understood as meaning silylated hydroxyl groups, for example those which occur in tri-lower alkylsilyloxy groups, such as trimethylsilyloxy or dimethyl-tert.-butylsilyloxy groups, or phenyl-di-lower alkylsilyloxy or lower alkyl-diphenylsilyloxy groups.

An esterified hydroxyl group can be derived both from an inorganic and an organic acid. Examples of the corresponding inorganic acids are sulphuric and phosphoric acids, and, in particular, hydrohalic acids, such as hydrofluoric, hydrochloric, hydrobromic and hydriodic acid. In a hydroxyl group esterified with an organic acid, the hydrogen atom of the hydroxyl group is replaced by the acyl group Ac. An esterified hydroxyl group can also be a lactonised hydroxyl group.

The acyl group Ac is derived from an organic acid and has one of the meanings assigned to the symbol $Ac^1$ hereinafter or represents the monovalent radical of an acyclic, carbocyclic or heterocyclic sulphonic acid, preferably one having not more than 18 carbon atoms, for example in particular an optionally halogenated lower alkanesulphonyl group, such as the methanesulphonyl and trifluoromethanesulphonyl group, a substituted or unsubstituted cycloalkanesulphonyl group, such as a camphor-10-sulphonyl group, or a benzenesulphonyl group which is unsubstituted or substituted by halogen, nitro, lower alkoxy and/or lower alkyl, such as the benzenesulphonyl, p-toluenesulphonyl (i.e. tosyl), p-chlorobenzenesulphonyl, p-bromobenzenesulphonyl and 2,4-dinitrobenzenesulphonyl group.

The acyl group $Ac^1$ is the monovalent radical derived from a hemiderivative of carbonic acid, from a carboxylic acid or from formic acid, i.e. the formyl group, and an analogous radical which contains sulphur instead of oxygen. The acyl radical of a hemiderivative of carbonic acid is in particular the acyl radical of a corresponding hemiester, for example preferably a lower alkoxycarbonyl or aryl-lower alkoxycarbonyl group which is unsubstituted or substituted in particular by lower alkyl, lower alkoxy, nitro and/or halogen, such as methoxycarbonyl, ethoxycarbonyl, tert.-butoxycarbonyl, 2,2,2-trichloroethoxycarbonyl, 2-iodoethoxycarbonyl, benzyloxycarbonyl, 2-phenyl-2-propoxycarbonyl, 2-p-tolyl-2-propoxycarbonyl, 2-p-biphenylyl-2-propoxycarbonyl, 1,1-diphenylethoxycarbonyl or p,p'-dimethoxybenzhydryloxycarbonyl group. Acyl radicals of the following derivatives of carbonic acid are also to be mentioned: a carbamoyl, carbazoyl, ureidocarbonyl or guanidino group, in which the nitrogen atoms can be partly or completely subtituted by hydrocarbon radicals, as well as corresponding thio analogues, as in particular a thiocarbamoyl or thiocarbazoyl group which is unsubstituted or substituted by one or two hydrocarbon radicals. The acyl radical of a carboxylic acid is a radical in which one of the above defined substituted or unsubstituted acyclic, carbocyclic, carbocyclic-acyclic, heterocyclic and heterocyclic-acyclic radicals is bonded to the carbonyl group. Acyl radicals of the following monocarboxylic acids having not more than 18 carbon atoms are particularly preferred: acyclic carboxylic acids, in particular lower alkanecarboxylic acids, such as propionic, butyric, isobutyric, valeric, isovaleric, capronic, trimethylacetic, enanthic and diethylacetic acid, and, most preferably, acetic acid, but also corresponding halogenated lower alkanecarboxylic acids, such as chloroacetic acid, bromoacetic acid or α-bromoisovaleric acid; carbocyclic or carbocyclic-acyclic monocarboxylic acids, for example cyclopropane-, cyclobutane-, cyclopentane- and cyclohexanecarboxylic acid and cyclopropyl-, cyclobutyl-, cyclopentyl- or cyclohexylacetic acid or cyclopentyl- or cyclohexylpropionic acid; aromatic carbocyclic carboxylic acids, for example benzoic acids which are unsubstituted or substituted by halogen, such as fluorine, chlorine or bromine atoms, and/or by hydroxyl, lower alkoxy, lower alkyl and nitro groups; aryl- or aryloxy-lower alkanecarboxylic acids and the analogues thereof which are unsaturated in the chain, for example phenylacetic or phenoxyacetic acids which are unsubstituted or substituted by the same substituents as indicated above for benzoic acid, phenylpropionic acids and cinnamic acids; and also heterocyclic acids, for example furane-2-carboxylic acid, 5-tert.-butylfurane-2-carboxylic acid, 5-bromofurane-2-carboxylic acid, thiophene-2-carboxylic acid, nicotinic or isonicotinic acid, 3-(4-pyridyl)-propionic acid, and pyrrol-2- or -3-carboxylic acids which can be substituted by lower alkyl groups, and corresponding α-aminoacids, in particular α-amino-lower alkanecarboxylic acids, for example glycine, phenylglycine, proline, leucine, valine, tyrosine, histidine and asparagine.

A bivalent acyl radical $Ac^2$ is derived chiefly from a dicarboxylic acid having not more than 18 carbon atoms which in turn is derived from the above optionally substituted acyclic, carbocyclic, carbocyclic-acyclic, heterocyclic and heterocyclicacyclic radicals in that it carries two carboxyl groups, optionally also at the heteroatoms. Examples of such dicarboxylic acids are: oxalic acid, malonic acid, mono- or di-lower alkylmalonic acid, succinic acid, glutaric acid, adipic acid, maleic acid, itaconic acid, citraconic acid, angelic acid, 1,1-cyclopentane- or 1,1-cyclohexane-dicarboxylic acid, a phthalic, quinolic or phenylsuccinic acid which is unsubstituted or substituted by halogen atoms, such as fluorine, chlorine or bromine atoms, and/or lower alkyl, lower alkoxy and nitro groups, and also tartronic acid, mesoxalic acid, oxalacetic acid, malic acid, tartaric acid, a tartaric acid which is esterified or etherified at the hydroxyl groups, glutamic acid and aspartic acid and derivatives of these last two acids with protected amino groups. $Ac^2$ can also be divalent radical of orthocarbonic acid or of an ortho-carboxylic acid, in particular a di-lower alkoxymethylene group, or a 1-lower alkoxyalkylidene or α-lower alkoxybenzylidene group, for example methoxymethylene, 1-methoxyethylidene, ethoxymethylene, 1-ethoxyethylidene, α-methoxybenzylidene and α-ethoxybenzylidene group.

An esterified carboxyl group is one in which the hydrogen atom is replaced by one of the hydrocarbon radicals referred to above, preferably a lower alkyl or phenyl-lower alkyl radical. An esterified carboxyl group is for example the methoxy-, ethoxy-, tert.-butoxy- or benzyloxycarbonyl group, and also a lactonised carboxyl group.

Of particular interest are also esters of carboxylic acid groups which are derived from polyhydric alcohols, for example from lower alkanediols, such as in particular from ethylene glycol or propylene glycol and glycerol.

Finally, mention is also to be made of esters of carboxylic acid groups which contain an alcohol component which can easily be removed by reduction, such as the p-nitrobenzyl radical. Ethers of the present invention with such esterified carboxyl groups are of particular importance as intermediates for obtaining the corresponding ethers which contain a free carboxyl group.

A primary amino group is a group of the formula -NH$_2$. An acylamino group corresponding to this group has the formula -NH-Ac, wherein Ac is as defined above, and a corresponding diacylamino group carries two monovalent acyl groups Ac which can be the same or different, or a bivalent acyl group Ac$^2$. A secondary amino group carries in place of one of both hydrogen atoms a monovalent hydrocarbon radical in which one or more carbon atoms can be replaced by heteroatoms, for example one of the above radicals. An acylamino group derived therefrom carries in addition the monovalent acyl group Ac defined above. A tertiary amino group carries two such monovalent hydrocarbon radicals (including the analogous heterocyclic radicals), which can be alike or different. If the amino group carries two substituents of the same or different kind (i.e. hydrocarbon radicals and/or acyl radicals), these substituents can be linked to each other through a C—C bond or by an oxygen, sulphur or substituted or unsubstituted nitrogen atom, and together with the nitrogen atom of the amino group can form a nitrogen-containing heterocyclic ring. Examples of especially preferred amino and acylamino groups are: lower alkylamino or di-lower alkylamino, such as methylamino, ethylamino, dimethyl-amino or diethylamino groups, and pyrrolidino, piperidino, morpholino, thiomorpholino and piperazino or 4-methylpiperazino groups, phenylamino, diphenylamino and benzylamino, which are unsubstituted or substituted by lower alkyl, lower alkoxy groups, halogen atoms and/or nitro groups. Acylamino is in particular carbamoylamino, carbazoylamino, mono- and di-lower alkylcarbamoylamino, such as mono- and dimethylcarbamoylamino, lower alkoxycarbonylamino, for example methoxycarbonylamine, ethoxycarbonylamino or tert.-butyloxycarbonylamino, halogen-lower alkoxycarbonylamino, such as 2,2,2-trichloroethoxycarbonylamino, phenyl-lower alkoxycarbonylamino, such as 4-methoxybenzyloxycarbonylamino, lower alkanoylamino, such as formylamino, acetylamino or propionylamino, and succinimido, glutarimido and phthalimido, and also 2-oxopyrrolidino, 2-oxopiperidino and 2-oxoperhydroazepino, which are derived from γ-butyro-, δ-valero and ε-caprolactam, as well as benzenesulphonylamino groups which are unsubstituted or substituted by halogen atoms, such as fluorine, chlorine and bromine atoms, and/or lower alkyl, lower alkoxy and nitro groups, such as the benzenesulphonylamino, p-toluenesulphonylamino (tosylamino) and p-bromobenzenesulphonylamino group. The above definition also relates to amino groups which are a constituent of other functional groups, such as carbamoyl, carbazoyl, ureido, guanidino, hydrazino, semicarbazido, semicarbazono or sulphamoyl groups. The term "lower" is used herein to denote radicals containing 1 to 7 carbon atoms.

Of the substituents listed above, the following are to be singled out for special mention: halogens, and in particular iodine, chlorine or bromine, and the cyano group CN; the free carboxyl group or the carboxyl group which is esterified with a lower aliphatic mono- or polyhydric alcohol of 1 to 7 carbon atoms, for example those singled out for special mention above; the carbamide group and the N-monoalkyl or di-lower alkyl derivatives thereof, wherein the lower alkyl groups preferably contain 1 to 7 carbon atoms and can contain a hydroxyl group or a further amino group at one or more carbon atoms which are not adjacent to the amide nitrogen, that is to say carbamide groups which are derived from lower alkanolamines or diamines; and also oxo, hydroxyl, alkoxy, aminoalkoxy groups, wherein the alkyl moieties again preferably contain 1 to 7 carbon atoms. An oxo group can be in the terminal position with respect to the cited saturated or unsaturated aliphatic hydrocarbon radicals as aldehyde group or at an intermediary carbon atom to form a ketone group. Among the compounds which contain several functional groups, hydroxycarboxylic acid and ketonecarboxylic acid groups must for example be mentioned. The carboxyl group and the functional derivatives thereof, such as the esters or amides, for example the groups mentioned above or hereinafter and the cyano group can be regarded as polyfunctional derivatives of the methyl group, and accordingly K itself in formula III can represent one of these radicals.

Examples of carbamide radicals are: the free carbamide group, N-mono- and di-lower alkylcarbamide groups, N-(hydroxy-lower alkyl)-carbamide groups and N-(amino-lower alkyl)-carbamide groups, the alkyl moieties of which contain 1 to 7 carbon atoms, in particular the N-methylcarbamide group, the N,N-dimethylcarbamide group, the N-ethylcarbamide group, the 2-hydroxyethylcarbamide group or the 2-aminoethylcarbamide group.

The above mentioned preferred radicals are present in particular in the aliphatic part of the hydrocarbon K, but they can also be present in the alicyclic part and particularly in the aromatic rings. Further preferred substituents of the aromatic rings are the nitro group, the amino group or sulphonic acid group.

In particular, the following groups of the new ethers of the present invention are to be mentioned: (a) ethers of formula (III) in which K represents an unsubstituted unsaturated aliphatic hydrocarbon radical of 1 to 7 carbon atoms, or a saturated or unsaturated hydrocarbon radical of 1 to 7 carbon atoms which is substituted by at least one of the functional substituents last singled out for special mention herein; (b) ethers of one of the above formulae (V), (VI) or (VII), in which K or one of the groups $A_1$, $—Kw_1—A_1$ and $Kw_2—A_2—Kw_3$ is unsubstituted or substituted by one or more of the functional substituents last singled out for special mention herein, and in which the groups $Kw_1$, $Kw_2$ and $Kw_3$ contain 1 to 7 carbon atoms. In particular, these last mentioned radicals are saturated hydrocarbon radicals.

Among the ethers of the above groups (a) and (b), again those compounds are to be singled out for special mention in which a free, esterified or amidated carboxyl group or a cyano group is present as substituent, taking into account in particular the above mentioned ester or amide groups which are particularly suitable. Especial mention is to be made of ethers in which K represents one of these groups.

Among the ethers of the present invention, a distinction must be made between the 12-monoethers and the 10,12-diethers on the one hand, and the 10-monoethers on the other. The former are obtained usually during the direct alkylation of Papulacandin A or B, as described in more detail hereinafter, whereas in general the 10-monoethers are not obtainable by this direct route in satisfactory yield.

10-Monoethers are therefore usually obtained indirectly by way of the diethers by preparing such diethers in which the phenolic 12-OH group is etherified with a readily and selectively removable group. Such a removable ether group is for example the p-nitrobenzyl group and the p-aminobenzyl group. These radicals can be readily split off by reduction to form the phenol group. The 12-p-nitrobenzyl and p-aminobenzyl ethers, in which the phenol group is etherified in the 10-position with any other ether radical, in particular one of those singled out for special mention above, are especially important, because they constitute starting materials for the 10-monoethers of the present invention.

The 10-monoethers of Papulacandin A and B have a particularly pronounced antifungal action and accordingly they constitute a preferred object of the present invention. Chiefly, 10-monoethers of Papulacandin A and B, especially of Papulacandin B, are prepared, which have the preferred ether groups mentioned above.

The use of Papulacandin B is also preferred for obtaining the 12-monoethers and 10,12-diethers.

Particularly interesting ethers of Papulacandin of the present invention are also those in which the ether groups have functional groups which are capable of salt formation, for example carboxyl groups and amino groups and basic heterocyclic substituents, since many of these salts are readily soluble in water.

Important metal salts of ethers which contain acid groups are in particular those of alkalies, for example of sodium or potassium, and also of calcium or magnesium, because they dissolve readily in water and can thus be used for the preparation of aqueous injection solutions. The water-solubility of ethers which contain basic groups can be attained by preparing acid addition salts and also quaternary ammonium salts. Therapeutically useful acids are used, such as hydrohalic acids, sulphuric acids, phosphoric acids, nitric acid, perchloric acid, aliphatic, alicyclic, aromatic or heterocyclic carboxylic or sulphonic acids, such as formic, acetic, propionic, succinic, glycolic, lactic, malic, tararic, citric, ascorbic, maleic, hydroxymaleic or pyruvic acid; phenylacetic, benzoic, p-aminobenzoic, anthranilic, p-hydroxybenzoic, salicylic or p-aminosalicylic acid; embonic acid, methanesulphonic, ethanesulphonic, hydroxyethanesulphonic, ethylenesulphonic acid; halobenzenesulphonic, toluenesulphonic, naphthalenesulphonic acids or sulphanilic acid; methionine, tryptophane, lysine or arginine.

These or other salts of the new compounds, for example the picrates, can also be used for purifying the resulting bases by converting the bases into their salts, separating these latter and liberating the bases again from the salts. Because of the close relationship between the bases in the free form and in the form of their salts, what is stated in this specification in respect of the free bases also applies by analogy to the corresponding salts.

In comparison to the Papulacandin compounds initially mentioned, the ethers of Papulacandin A and B and their salts of the present invention constitute antimycotic and/or antiviral antibiotics with increased potency and/or different activity spectrum. They have a good antifungal action against yeast-like fungi, in particular against *Candida albicans, Candida tropicalis*, Trichophyton or Microsporum. Thus, for example, in the vitro examination in the agar dilution test according to the method of Ericsson and Sherris (1971) (Acta Path. Microbiol. Scand. Sektion B, Suppl. No. 217 79B, 1-90) they exhibit a good antimycotic action against *Candida albicans* or *Candida tropicalis* in the concentration range of 0.2–50 mcg/ml. The new compounds are distinguished by low toxicity in comparison with known antibiotics having antifungal action. They can therefore be used for controlling infections which are caused by the above fungi, in particular *Candida albicans*, and also as feed additive, for preserving foodstuffs or as disinfectants.

The new ethers of Papulacandin A and B possess in addition an antiviral action and can be used for obtaining e.g. preparations for topical application for controlling viral infections, for example Herpes virus hominis.

The ethers of the present invention of Papulacandin A and B can be prepared from Papulacandin A or Papulacandin B or from the monoethers thereof by the methods which are known per se for obtaining aromatic ethers, while preferably avoiding strong alkaline or acid conditions under which the Papulacandin molecule is not stable. The process of the present invention for the production of the new ethers accordingly comprises treating Papulacandin A or Papulacandin B or monoethers thereof, avoiding strong acid or alkaline conditions, with agents which are able to etherify phenolic hydroxyl groups, and, if desired, in resultant diethers optionally setting free an etherified hydroxyl group, and/or, if desired, in at least one of the ether radicals converting functional groups or setting them free from protective groups or converting them into one another.

Preferably, the above starting materials are reacted with a halogen compound $R_1X$ or $R_2X$, in which X represents a halogen atom, preferably an iodine or bromine atom, corresponding to the ether radical $R_1$ or $R_2$ to be introduced, in the presence of a base, in particular silver oxide or silver carbonate. Instead of the halogen compounds, however, it is also possible to use, if appropriate, the corresponding alcohols in the presence of an acid catalyst, such as a mineral acid, for example hydrochloric or sulphuric acid or preferably a Lewis acid, for example boron trifluoride or zinc fluoride.

Another preferred method of obtaining the ethers consists in reacting the starting materials with a diazoalkane. This method has practical significance only in those cases in which the diazo compound which corresponds to the ether group to be introduced can be easily prepared.

Another preferred method of producing the new ethers of the present invention is based on the nucleophilic attack of the phenolate ion when reacting the starting materials with an unsaturated compound in which the double bond is conjugated with an electronegative group, for example carboxyl, cyano, nitro. In this method, addition of the unsaturated compound to the phenolate ion in the form of a Michael addition to form a phenol ether takes place. The reaction is carried out preferably in the presence of dimethyl formamide. As unsaturated compounds it is possible to use for example acrylate, such as methyl or ethyl acrylate, or acrylonitrile.

The above discussed methods starting from Papulacandin A or B result usually in mixtures of the 12-monoether and the 10,12-diether. These mixtures can be separated in a manner known per se, for example by known physical separating methods, such as chromatography, crystallisation, partition between different phases and the like. The monoethers thereby obtained can also be reacted by the above described general methods to give diethers, for example by treatment with the halogen compound corresponding to the radical to be introduced in the presence of silver oxide. It is thus possible to obtain diethers with different ether radicals $R_1$ and $R_2$.

The above mentioned and especially preferred 10-monoethers can be prepared from the diethers just discussed with different radicals $R_1$ and $R_2$, in which the ether radical $R_1$ in the 12-position is a radical which can be reduced under mild conditions, in particular the p-nitrophenyl radical, which accordingly can be removed selectively. The reduction of the p-nitrobenzyl group can be carried out for example with zinc/glacial acetic acid in the presence of a lower aliphatic alcohol, for example an alkanol of 1 to 7 carbon atoms, such as methanol or ethanol, or of a lower aliphatic nitrile, such as acetonitrile, at low temperature or at room temperature, for example between 0° and 23° C.

The reaction of the starting materials with the above alkylating agents is carried out in a manner known per se, for example between approx. 0° and approx. 60° C., for example at room temperature, in the solvents ordinarily used for this reaction and with or without the addition of conventional catalysts. Accordingly, in the reaction with a halogen compound $X-CH_2-K$ and silver oxide, wherein K has the above meaning and X represents bromine or iodine, the reaction is advantageously carried out in dimethyl formamide at 0° C. or room temperature, using for example between 5 and 25 equivalents of silver oxide and between 5 and 50, for example 10 and 25, equivalents of the halogen compound. The reaction is complete usually between approx. 50 minutes and 3 hours. Other suitable solvents are ethers, for example tetrahydrofurane or dioxane.

The optional conversion of functional groups into the ether radicals is carried out by methods which are known per se, but only those methods are employed which leave the structure of the Papulacandin skeleton intact. Accordingly, for example, strong alkaline or acid conditions should be avoided.

In particular, the functional groups containing the nitrobenzyl group, for example a carboxyl group esterified with nitrobenzyl alcohol, as described above for the reduction of the p-nitrobenzyl radical, can be reduced.

Functional groups which are present in the ether radicals, such as hydroxyl groups or amino groups, can be acylated, for example in a manner known per se. Carboxyl groups can be converted in a manner known per se into their esters or amides. Conversely, ester groups, for example readily saponifiable esters groups, such as the trifluoroacetate group, can be optionally converted into the free hydroxyl groups. Amino groups can, if desired, be alkylated and/or converted into the quaternary ammonium salts.

As initially mentioned, the starting materials Papulacandin A and B can be obtained by culturing the strain NRRL No. 8086.

The antibiotic Papulacandin is formed when culturing the species *Papularia sphaerosperma*, in particular the strain NRRL 8086. Papulacandin is obtained by culturing *Papularia sphaerosperma*, or a mutant that forms Papulacandin, aerobically in an aqueous nutrient solution which contains a source of carbon or nitrogen and inorganic salts until the nutrient solution displays a substantially antibiotic action, and subsequently isolating the antibiotic Papulacandin. The mutants that form the antibiotic Papulacandin can be obtained, for example, under the action of ultraviolet rays or X-rays or from nitrogen-mustard oils. Preferably the strain NRRL 8086 (A 32283) is used.

Examples of carbon sources are: assimilable carbohydrates, for example glucose, saccharose, lactose, mannitol, starch, glycerol, and also inositol. As nitrogen-containing nutrients there may be mentioned: amino acids, peptides and proteins and their degradation products, such as peptone or tryptone, meat extracts, water-soluble constituents of cereal grains, such as maize and wheat, of distillation residues of alcohol production, of yeast, beans, especially of the soya bean plant, of seeds, for example of the cotton plant, and also ammonium salts and nitrates. Of other inorganic salts the nutrient solution can contain, for example, chlorides, carbonates, sulphates, phosphates of alkali metals or alkaline earth metals, of magnesium, iron, zinc and manganese.

The cultivation is carried out aerobically, that is to say, for example, in a quiescent surface culture or preferably immersed while being agitated or stirred with air or oxygen in a shaking flask or a known fermenter. A suitable temperature is one between 18° and 40° C., preferably app. 23° C. As a rule, the nutrient solution exhibits a substantially antibacterial action after 1½ to 5 days. It is preferable to carry out the cultivation in several steps, i.e. to prepare initially one or more precultures in a liquid nutrient medium and then to inoculate the actual production medium with these, for example in the ratio 1:20. The preculture is obtained, for example, by inoculating a liquid medium with a spored mycelium obtained by an approximately 14 day growth on a solid culture medium and allowing it to develop. The antibiotic is isolated from the culture medium by methods which are known per se, taking into account the chemical, physical and biological properties of the antibiotic.

Thus the antibiotic can be extracted from the unfiltered culture broth with an organic solvent which is sparingly soluble in water, for example ethyl acetate. This "whole broth" process is preferably used, because the antibiotic is present both in the mycelium and in the culture filtrate. The antibiotic collects in the organic phase, for example in the ethyl acetate, and this phase is separated from the extracted culture liquid and the "slurry" (extracted mycelium and solid constituents of the nutrient solution). The residue obtained during the extraction can be subjected to one or more repeated extractions with the same solvent or with another solvent.

The mycelium which is filtered off, for example, with filter aids, or the culture filtrate, can also be extracted alone. The mycelium which has been washed with water (together with the filter aid) is preferably extracted with a water-miscible organic solvent, for example a lower alkanol containing 1 to 4 carbon atoms, such as methanol, ethanol, propanol, isopropanol, dimethyl sulphoxide, formamide, dimethyl formamide, methyl acetamide, dioxan, tetrahydrofuran, acetone, or with mixtures of these solvents with water, in particular with aqueous methanol. The culture filtrate is extracted with a water-immiscible solvent, for example ethyl acetate, a water-immiscible alcohol, for example n-butanol, or a higher aliphatic ketone, for example methyl isopropyl.

After the solvent has been evaporated off, the crude product obtained can be purified, for example, by extraction, precipitation, partitioning between immiscible solvent phases, or by absorption, above all by chromatography. It is thus possible to remove from the crude product, for example the ethyl acetate extract of the culture broth, substantial amounts of impurities by successive simple purification methods, such as extraction of the dried or dissolved crude product with solvents in which the antibiotic is insoluble, for example hydrocarbons such as petroleum ether, cyclohexane, or anhydrous halogenated hydrocarbons, for example methylene chloride, chloroform, carbon tetrachloride. It is also possible to dissolve the crude product, for example in methanol, and to remove impurities from it by adsorption agents, such as activated charcoal, silica gel, magnesium silicate, aluminium oxide, or mixtures thereof, or by adsorption resins, for example crosslinked dextranes such as "Sephadex" ® (Pharmacia Fine Chemicals, Uppsala). The crude product can be purified, for example, by repeated column chromatography using silica gel, advantageously with the addition of small amounts of activated charcoal. The antibiotic is eluted preferably by the gradient method with mixtures of chloroform or carbon tetrachloride and methanol, the percentage content of the stronger polar solvent being increased gradually. When the extract obtained by extraction of the culture broth is chromatographed through a mixture of silica gel with, for example, 5 percent by weight of activated charcoal and, for example, chloroform/methanol as eluant, virtually the entire amount of the antibiotic extracted from the culture broth is found in the eluates of the methanol concentrations 5–20%.

The above distribution between immiscible solvent phases can also be carried out as counter-current distribution in a Craig apparatus. A mixture of ethyl acetate, cyclohexane, methanol and water is used, for example, as solvent system.

The individual unitary components of the antibiotic can be obtained by separating and isolating them by preparative thin-layer chromatography under the conditions described for analytical proof. The separation by means of column chromatography is more advantageous, using for example silica gel which contains 1 to 5% of activated charcoal and effecting elution preferably by the gradient method with a mixture of chloroform and methanol. The increase in the concentration of the more polar solvent is advantageously effected in smaller percentage amounts, for example 5–20% of methanol, or the continuous gradient elution method is used. The antibiotic is preferably eluted at a methanol concentration of 10%. The purification procedure can be repeated, if appropriate.

When carrying out thin-layer chromatography over silica gel (e.g. with chloroform/methanol or ethyl acetate/acetone/water as eluant) and effecting biautography with Candida albicans, it is possible to isolate at least five active components with antibiotic action whose Rf values in a thin-layer chromatogram on silica gel are reported in Table I. System 1 denotes chloroform/methanol (4:1), two developments, and system 2 denotes ethyl acetate/acetone/water (72:24:4), two developments.

TABLE I

| Substance | System 1 | System 2 |
|---|---|---|
| Papulacandin | | |
| component A | 0.35 | 0.41 |
| component B | 0.27 | 0.32 |
| component C | 0.24 | 0.28 |
| component D | 0.45 | 0.74 |
| component E | 0.47 | 0.51 |

App. 70% of the antibiotic consists of the main component B, app. 20% of component A.

The antibiotic Papulacandin B possesses the following chemical and physical properties: It is a weakly acid substance, which is white when in powder form. It is soluble in alcohols, for example lower alkanols, such as methanol, ethanol, n-propanol, and in ketones, for example di-lower alkyl ketones, such as acetone, methyl, isobutyl ketone, and also in dimethyl formamide and dimethyl sulphoxide. The compound is sparingly soluble in ethyl acetate and chlorinated hydrocarbons, such as methylene chloride, chloroform and carbon tetrachloride (10–100 mg/l), and is virtually insoluble in water, petroleum ether, hexane. Melting point: 193°–197° C. (with decomposition).

Elementary analysis (calculated for $C_{47}H_{64}O_{17}$): C calc: 62.65%; found: 61.69% H found: 7.16%; calc: 7.18%. $[\alpha]_D^{20} = +50.0 + 1°$ (c=0.46 in methanol).

UV-spectrum in ethanol:
$\lambda$max
232 nm ($\epsilon$=42 000)
240 nm ($\epsilon$=42 400)
268 nm ($\epsilon$=44 800)
300 nm ($\epsilon$=31 200).

IR spectrum in KBr, see Example 3.
360 MHz—NMR-spectrum, see FIG. 1.

The antibiotic Papulacandin component A has the following chemical and physical properties: it is a weakly acid, white substance, when in crystalline form, with the same solubility properties as component B. Melting point: 171°–173° C. (with decomp.).

Elemental analysis (calculated for $C_{47}H_{66}O_{16}$): C found: 62.29: C calc: 63.64: H found: 7.54 H calc: 7.50

UV spectrum (in ethanol):
$\lambda$max
232 nm shoulder
242 nm ($E_{max}$=425)
265 nm ($E_{max}$=520)

IR-spectrum in KBr, see Example 1
$[\alpha]_D^{20} = +30 \pm 1°$ (c=0.419 in methanol).
360 NHz—NMR-spectrum, see FIG. 2.

| 13 C-NMR data of Papulacandin B | |
|---|---|
| Assignment | ppm |
| C(1″) and | 169,1 |
| C(1‴) | 168,5 |
| C(10) | 161,6 |
| C(12) | 154,5 |
| C(8″) | 146,1 |
| C(8) | 145,5 |
| | 143,6 |
| | 141,7 |
| | 141,0 |
| | 138,7 |
| | 137,6 |
| olefinic | 136,2 |
| C-atoms | 131,6 |
| | 127,1 (3C) |
| | 125,4 |
| | 122,2 |
| | 121,7 |

-continued

| 13 C-NMR data of Papulacandin B | |
|---|---|
| Assignment | ppm |
| C(9) | 116,5 |
| C(1) | 112,0 |
| C(1') | 105,4 |
| C(13) | 103,1 |
| C(11) | 100,1 |
| | 77,6 (2C) |
| | 76,5 |
| C(7'') | 74,8 |
| C(8''') | 74,1 (2C) |
| C(2) to C(5) | 74,0 (2C) |
| C(2') to C(5') | 72,6 |
| | 71,9 |
| | 70,4 |
| C(6') | 64,9 |
| C(6) | 61,6 |
| C(6'') | 40,1 |
| C(14'') | 37,6 |
| C(13'') | 35,3 |
| C(12'') | 31,6 |
| C(9''') | 31,0 |
| C(15'') | 30,5 |
| C(18'') | 19,5 |
| C(17'') | 12,3 |
| C(16'') | 11,7 |
| C(10''') | 10,2 |

The new ethers of Papulacandin A and B of the present invention can be used, as already mentioned, as a medicine, for example in the form of pharmaceutical preparations. These preparations contain the compounds of the present invention mixed with a pharmaceutical organic or inorganic carrier which is suitable for topical, enteral or parenteral application. Suitable carriers are those substances that do not react with the compound of the present invention, for example gelatin, lactose, starch, magnesium stearate, vegetable oils, benzyl alcohols, or other known medicinal carriers. The pharmaceutical preparations can be in the form of tablets, coated tablets, powders, suppositories, or in liquid form as solutions, suspensions, emulsions, creams or ointments. Where appropriate they are sterilised, and/or contain assistants, such as preservatives, stabilisers, wetting agents or emulsifiers. They can also contain other therapeutically useful substances. The feed additives, preservatives and disinfectants can also be mixed, as known, with suitable carriers.

In particular, pharmaceutical preparations for topical application are suitable, for example creams, ointments, gels, pastes, foams, tinctures and solutions, which contain the active substance in an amount between approx. 0.005 and approx. 1% by weight.

Creams are oil-in-water emulsions which contain more than 50% of water. Fatty alcohols are chiefly used as oleaginous base, for example lauryl, cetyl or stearyl alcohol, fatty acids, for example palmitic or stearic acid, liquid to solid waxes, for example isopropyl myristate, wool wax or bees-wax, and/or hydrocarbons, for example petroleum jelly (petrolatum) or paraffin oil. Suitable emulsifiers are surface-active substances with primarily hydrophilic properties, such as corresponding non-ionic emulsifiers, for example fatty acid esters of polyalcohols or ethylene oxide adducts thereof, such as polyglycerol fatty acid esters or polyoxyethylene sorbitan fatty acid esters (Tweens); polyoxyethylene fatty alcohol ethers or esters; or corresponding ionic emulsifiers, such as alkali metal salts of fatty alcohol sulphates, for example sodium lauryl sulphate, sodium cetyl sulphate or sodium stearyl sulphate, which are customarily used in the presence of fatty alcohols, for example cetyl alcohol or stearyl alcohol. Additives to the water phase include agents which reduce water less through evaporation, for example polyalcohols, such as glycerol, sorbitol, propylene glycol and/or polyethylene glycols, as well as preservatives, perfumes etc.

Ointments are water-in-oil emulsions which contain up to 70%, preferably however approx. 20% to about 50%, of water or aqueous phase. The oleaginous phase comprises chiefly hydrocarbons, for example petroleum jelly, paraffin oil and/or hard paraffins, which contain preferably hydroxy compounds suitable for improving the water-absorption, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the water phase include humectants, such as polyalcohols, for example glycerol, propylene glycol, sorbitol and/or polyethylene glycol, and preservatives, perfumes etc.

Greasy ointments are anhydrous and contain as base in particular hydrocarbons, for example paraffin, petroleum jelly and/or liquid paraffins, furthermore natural or partially synthetic fat, for example coconut fatty acid triglycerides, or preferably hardened oils, for example hydrated ground nut or castor oil, and also fatty acid partial esters of glycerol, for example glycerol mono- and distearate, and, for example, the fatty alcohols, emulsifiers and/or additives for increasing the water-absorption mentioned in connection with the ointments.

Pastes are creams and ointments containing powdered ingredients which absorb secretions, such as metal oxides, for example titanium oxide or zinc oxide, and talc and/or aluminium silicates whose purpose it is to bind moisture or secretion present.

Foams are administered from pressurised dispensers and are liquid oil-in-water emulsions in aerosol form, with halogenated hydrocarbons, such as chlorofluoro-lower alkanes, for example dichlorodifluoromethane and dichlorotetrafluoroethane being used as propellants. For the oleaginous phase there are used, inter alia, hydrocarbons, for example paraffin oil, fatty alcohols, for example cetyl alcohol, fatty acid esters, for example isopropyl myristate, and/or other waxes. As emulsifiers there are used, inter alia, mixtures of those emulsifiers with primarily hydrophilic properties, such as polyoxyethylene sorbitan fatty acid esters (Tweens), and those with primarily lipophilic properties, such as sorbitan fatty acid esters (Spans). In addition, the conventional additives are used, such as preservatives etc.

Tinctures and solutions generally have an aqueous ethanolic base to which are added, inter alia, polyalcohols, for example glycerol, glycols, and/or polyethylene glycol, as humectants for reducing water loss, and fat-restoring substances, such as fatty acid esters with lower polyethylene glycols, i.e. lipophilic substances which are soluble in the aqueous mixture as substitute for fatty substances which are taken from the skin with the ethanol, and, if necessary, other assistants and additives.

The pharmaceutical preparations for topical application are obtained in known manner, for example by dissolving or suspending the active substance in the base or in a part thereof, if necessary. When processing the active substance in the form of a solution, it is usually dissolved in one of the two phases before the emulsification, and when processing the active substance in the form of a suspension, it is mixed with a part of the base before the emulsification and then added to the remainder of the formulation.

The above process for the production of the new ethers of Papulacandin A and B also comprises those embodiments in which a start is made from any step and the missing steps are carried out or in which a starting material is formed under the reaction conditions.

The invention is illustrated by the following Examples.

EXAMPLE 1

A well-developed culture of *Papularia sphaerosperma* A 32283 on slant agar is suspended in 5 ml of 0.2 m-phosphate buffer at pH 7. Three Erlenmeyer flasks with 1 baffle and each containing 100 ml of nutrient solution which contains 20 g of soya bean flour and 20 g of mannitol per liter of tap water and the pH of which has been adjusted to 8.5 with normal sodium hydroxide solution before the sterilisation, are each inoculated with 5 ml of the Papularia suspension and incubated for 48 hours at 23° C. on a rotating shaking machine with a speed of 250 rpm. 25 ml of the culture obtained in this manner are put into each of 6 two liter Erlenmeyer flasks with 4 baffles and inoculated with 500 ml of the above nutrient solution. The flasks are then incubated at 23° C. on a rotating shaking machine (speed 120 rpm) for 48 hours. Then 1.5 liters of the culture from the 2 liter flasks are transferred to a 50 liter fermenter which contains 30 liters of the above nutrient solution and incubated for 48 hours at 23° C. Then 15 liters of the culture are transferred to a fermenter with 300 liters of the above nutrient solution. This fermenter has a total volume of 500 liters and is equipped with a 6-bladed turbine impeller and 4 baffles. The culturing conditions in the fermenter are: 1 atmosphere (gauge) pressure, stirring speed 450 rpm, temperature 23° C., air flow 1 liter V/V/min. The conditions correspond to an oxygen absorption rate of 200 mmoles of $O_2$/1hr measured in sulphite solution. The optimum formation of the antibiotic A 32283 takes place after app. 60 hours incubation. The culture solution then has a pH of 6.7. It has an activity of 10–12 mm inhibiting areola in the agar diffusion test with *Candida albicans* using Whatmann A discs with a diameter of 6 mm.

600 liters of the culture solution obtained in Example 1 are filtered while adding 2% of the filtering aid "Decalite" (diatomaceous earth). 560 liters of culture filtrate are adjusted to pH 8.6 and extracted twice with ethyl acetate in the ratio 2:1 in a continuous extractor. The inactive aqueous raffinate is discarded and 600 liters of ethyl acetate phase are concentrated in vacuo to yield a concentrate of 45 liters.

91 kg of mycelium from the above filtration are stirred once with 200 liters of methanol and once with 100 liters of methanol and filtered on each occasion. The inactive mycelium is discarded. Then 300 liters of methanol extract are concentrated in vacuo to yield an aqueous mycelium extract of 33 liters, which is adjusted to pH 8.4 with NaOH and extracted twice with 66 liters of ethyl acetate. The inactive raffinate is discarded.

Then 120 liters of mycelium-ethyl acetate extract are combined with the above 45 liters of culture filtrate-ethyl acetate extract and concentrated in vacuo to yield 1.85 liters of ethyl acetate extract concentrate, which is diluted with 2 liters of 85% methanol and extracted with 3% 2 liters of petroleum ether. The inactive petroleum ether phases are discarded and the methanol phase is evaporated to dryness in vacuo to yield 51 g of dark brown viscous residue, which is dissolved in 200 ml of 85% methanol and extracted with 2×300 ml of heptane. The inactive heptane phases are discarded. The methanol phase is concentrated and dried in vacuo.

Yield: 41.8 g of extract residue.

18 g of the extract residue are chromatographed through a column (diameter: 5.4 cm, height: 140 cm) which consists of a mixture (95:5 weight ratio) of 1000 g of silica gel (Merck, granular size 0.05–0.2 mm) and 50 g of activated charcoal Norit ®. The mixture of silica gel/activated charcoal was suspended beforehand 3 times in methanol and subsequently 3 times with chloroform and filtered. The 12.3 g of extract of residue are dissolved in 50 ml of methanol, mixed with 50 g of silica gel and the mixture is evaporated to dryness. The dried powdery residue is added to the column. The elution is performed in fractions of 1 liter each with chloroform-methanol mixtures while gradually increasing the concentration of methanol, beginning with a methanol content of 4% and ending with 50%. The rate of flow is 500 ml/hr. The fractions are concentrated in vacuo and the residue is dried in a high vacuum. The fractions are then combined on the basis of thin-layer chromatographic and bioautographic examination. Fractions 1–16 (eluted with 1–4% methanol) are only weakly active and are discarded. Fractions 17–23 (eluted with 4 to 7% methanol) contain Papulacandin D and E (further purification see Example 5). Fractions 24–27 (eluted with 7% methanol) contain Papulacandin A. Fraction 28 (eluted with 10% methanol) contains a mixture of Papulacandin A and B. Fractions 29–31 (eluted with 10% methanol) contain Papulacandin B. Fractions 32–36 (eluted with 10–20% methanol) contain Papulacandin G with smaller Rf value in addition to Papulacandin B. The remaining fractions (eluted with 20–50% methanol) contain still further active substances in small amounts.

To isolate Papulacandin B, the residue of the fractions 29–31 (0.86 g) is crystallised from acetonitrile or precipitated from acetone/ether/hexane, affording 1.5 g of pure Papulacandin B as colourless crystals or as a colourless powder which melts at 171°–173° C. (with decomposition). To isolate Papulacandin A, the residue of the fractions 24–27 (1.5 g) is crystallised from acetone or precipitated from acetone/hexane, affording 1.2 g of pure Papulacandin A as colourless crystals or as a powder which melts at 171°–173° C.

EXAMPLE 2

1 g of Papulacandin B, 2.65 g of silver oxide (10 equivalents) and 3.4 g of allyl bromide (10 equivalents) are intensively stirred in 100 ml of dimethyl formamide for 50 minutes at room temperature until Papulacandin B can no longer be detected by thin-layer chromatography. The reaction solution is filtered over Celite and thereafter evaporated to dryness in vacuo. The residue is taken up in methanol, filtered once more over Celite and evaporated to dryness. The crude product is subsequently dissolved in chloroform and chromatographed on a column of 100 g of silica gel. The column is eluted with chloroform containing increasing proportions of methanol (2–20%). The fractions containing the desired product as determined by thin-layer chromatography are combined. Precipitation from acetone/ether/hexane yields Papulacandin B-10,12-diallyl ether as a colourless amorphous powder.

Rf-value: 0.42 in CHCl$_3$—CH$_3$OH—(4:1); UV: $\lambda_{max}$. ($\epsilon$) (ethanol): 235 nm (38 000), 264 nm (37 600), 297 nm shoulder; IR; 3500, 2950, 1705, 1620, 1465, 1430, 1380, 1345, 1305, 1265, 1150, 1065, 1035, 1005, 870 cm$^{-1}$.

The fractions which contain Papulacandin B-12-monoallyl ether are combined and concentrated. Precipitation from acetone/ether/hexane yields Papulacandin B-12-monoallyl ether as a colourless amorphous powder.

$^{13}$C-NMR: 71.8 ppm (—O—CH$_2$—CH=CH$_2$), 156.14 ppm (C-12), 161.74 ppm (C-10).

EXAMPLE 3

1.45 g of Papulacandin B, 3.84 g of silver oxide (10 equivalents) and 12.76 g of 1,3-diiodopropane (25 equivalents) are intensively stirred in 150 ml of dimethyl formamide for 3½ hours until Papulacandin B can no longer be detected by thin-layer chromatography. The reaction solution is then filtered over Celite and evaporated to dryness in vacuo. The residue is dissolved in methanol, filtered once more over Celite and again evaporated to dryness. The crude product is subsequently dissolved in chloroform and chromatographed on a column of 100 g of silica gel. The column is eluted with chloroform containing increasing proportions of methanol (5–20%). The fractions containing the desired product as determined by thin-layer chromatography are combined. Precipitation from acetone/ether/hexane yields Papulacandin B-10, 12-mono-iodopropyl ether as a colourless amorphous powder.

Papulacandin B-12-mono-iodopropyl ether

Rf-value: 0.45 in CHCl$_3$—CH$_3$—OH—(4:1) UV: $\lambda_{max}$. ($\epsilon$) (ethanol): 235 nm (40 000), 265 nm (40 500), 297 nm (28 500).

IR: 3500,2950,1700,1615,1465,1425,1380,1345,1300,1265, 1150,1065,1030,1010,870 cm$^{-1}$.

$^{13}$C-NMR: 73.95 ppm (—O—CH$_2$—), 34,20 ppm (—O—CH$_2$—CH$_2$—), 2.70 ppm (—O—CH$_2$CH$_2$—CH$_2$—I).

Papulacandin B-10,12-diiodopropyl ether

Rf-value: 0.64 in CHCl$_2$—CH$_3$OH—(4:1)

UV: $\lambda_{max}$. ($\epsilon$) (ethanol): 231 nm (38 000), 265 nm (39 000), 295 nm shoulder.

IR: 3500,2950,1705,1620,1465,1425,1380,1350,1305,1265,1150, 1065,1030,1070,870 cm$^{-1}$.

$^{13}$C-NMR: 73.99 ppm (2×O—CH$_2$—CH$_2$CH$_2$—I), 34.28 and 34.01 ppm, (2×OCH$_2$—CH$_2$—CH$_2$—I), 2.68 and 2.47 ppm, (2×OCH$_2$CH$_2$CH$_2$—I).

EXAMPLE 4

5 g of Papulacandin B, 6.63 g of silver oxide (5 equivalents) and 3.8 g of bromacetone (5 equivalents) are intensively stirred in 500 ml of dimethyl formamide for 1½ hours at 0° C. until Papulacandin B can no longer be detected by thinlayer chromatography. The reaction solution is filtered over Celite and thereafter evaporated to dryness in vacuo. The residue is taken up in methanol, filtered once more over Celite and evaporated to dryness. The crude product is subsequently dissolved in chloroform and chromatographed on 300 g of silica gel. The column is eluted with chloroform containing increasing proportions of methanol (2–20%). The fractions containing the desired product as determined by thin-layer chromatography are combined. Precipitation from acetone/ether/hexane yields Papulacandin B-10,12-di-(2'-oxopropyl) ether and Papulacandin B-12-mono-(2'-oxopropyl) ether as a colourless amorphous powder.

Papulacandin B-12-mono-(2'-oxopropyl) ether

Rf-value: 0.21 in chloroform-methanol-(4:1)

UV: $\lambda_{max}$. ($\epsilon$) (ethanol): 231 nm (32 000), 266 nm (34 400), 298 nm shoulder.

IR (in KBr): 3500,2950,1710,1020,1465,1430,1350,1265, 1155,1065 cm$^{-1}$.

$^{13}$C-NMR: 26.98 ppm (—CH$_2$CO—CH$_3$), 155.35 ppm (C-12), 161.52 ppm (C-10), 207.34 ppm (—CH$_2$—CO—CH$_3$.

$^1$H-NMR: 2.25 ppm

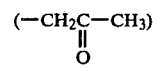

(—CH$_2$C—CH$_3$)
‖
O

Papulacandin B-10,12-di-(2'-oxopropyl) ether

Rf-value: 0.47 in chloroform-methanol-(4:1)

UV: $\lambda_{max}$. ($\epsilon$) (ethanol): 232 nm (34 400), 268 nm (35 200), 298 nm shoulder.

IR (in KBr): 3500,2950,1705,1620,1465,1430,1355, 1260,1155,1060 cm$^{-1}$.

| $^{13}$C—NMR: | 26.41 ppm | (—OCH$_2$CO CH$_3$) |
| --- | --- | --- |
| | 26.92 ppm | |
| | 69.54 ppm | (—OCH$_2$CO CH$_3$) |
| | 69.41 ppm | |
| | 155.43 ppm | (C-12) |
| | 162.47 ppm | (C-10) |
| | 206.71 ppm | (—OCH$_2$CO CH$_3$) |
| | 207.13 ppm | |

EXAMPLE 5

1.5 g of Papulacandin B, 1.98 g of silver oxide (5 equivalents) and 1.28 g of methylbromoacetate (5 equivalents) are intensively stirred in 150 ml of dimethyl formamide for 1¾ hours at room temperature until Papulacandin B can no longer be detected by thin-layer chromatography. The reaction solution is filtered over Celite and thereafter evaporated to dryness in vacuo. The residue is dissolved in methanol, filtered once more over Celite and evaporated to dryness. The crude product is subsequently dissolved in chloroform and chromatographed on 120 g of silica gel. The column is eluted with chloroform containing increasing proportions of methanol (2–20%). The fractions containing the desired product as determined by thin-layer chromatography are combined. Precipitation from acetone/ether/hexane yields Papulacandin B-10,12-di-(methoxycarbonylmethyl) ether and Papulacandin B-12-mono-(methoxycarbonylmethyl) ether as a colourless amorphous powder.

Papulacandin B-12-mono-(methoxycarbonylmethyl) ether

Rf-value: 0.46 in CHCl$_3$—CH$_3$OH—(4:1)

UV: $\lambda_{max}$. ($\epsilon$) (ethanol): 232 nm (35 200), 265 nm (37 200), 298 shoulder.

IR (in KBr): 3500,2970,1750,1710,1625,1450,1385, 1355,1270,1155,1070,1035,1010 cm$^{-1}$.

13C-NMR: 52.84 ppm (OCH2CO<u>O</u>CH3), 66.59 ppm (<u>OCH2</u>COOCH3), 155.56 ppm (C-12), 161.92 ppm (C-10), 171.26 ppm (OCH2<u>C</u>OO—CH3).

Papulacandin B-10,12-di-(methoxycarbonylmethyl) ether

Rf-value: 0.68 in CHCl3—CH3OH—(4:1)

UV: $\lambda_{max}$. ($\epsilon$) (Aethanol: 228 nm (30 400), 265 nm (30 400), 265 nm (32 300)

IR (in KBr): 3500,2960,1750,1710,1625,1500, 1450,1385,1355,1270,1170 cm$^{-1}$.

| 13C—NMR: | | |
|---|---|---|
| | 52.72 ppm | (OCH2COOCH3) |
| | 52.92 ppm | |
| | 66.34 ppm | (OCH2COOCH3) |
| | 66.67 ppm | |
| | 155.47 ppm | (C-12) |
| | 162.48 ppm | (C-10) |
| | 171.13 ppm | (2 × OCH2COOCH3) |

1H-NMR: 3.80 and 3.82 ppm (2×—COOCH3).

EXAMPLE 6

8 g of Papulacandin B, 10.4 g of silver oxide (5 equivalents) and 12.2 g of p-nitrobenzyl bromoacetate (5 equivalents) are intensively stirred in 500 ml of dimethyl formamide for 2½ hours at room temperature until all the starting material can no longer be detected by thin-layer chromatography. The reaction solution is filtered over Celite and thereafter evaporated to dryness in vacuo. The residue is taken up in methanol, filtered once more over Celite and evaporated to dryness. The crude product is subsequently dissolved in chloroform and chromatographed on a column of 250 g of silica gel. The column is eluted with chloroform containing increasing proportions of methanol (2–20%). The fractions containing the desired product as determined by thin-layer chromatography are combined. Precipitation from acetone/ether/hexane yields Papulacandin B-12-(p-nitrobenzyloxycarbonylmethyl) ether and Papulacandin B-10,12-di-(p-nitrobenzyloxycarbonylmethyl) ether as a colourless amorphous powder.

Removal of the p-nitrobenzyl group 1.5 g of Papulacandoin B-12-(p-nitrobenzyloxycarbonylmethyl) ether are dissolved in 70 ml of acetic acid and 30 ml of methanol. Then 3 g of zinc dust are added and the mixture is intensively stirred for 30 minutes at room temperature. The reaction soluton is filtered over Celite and subsequently evaporated to dryness in vacuo. The residue is dissolved in a small amount of methanol and the solution is diluted with water, and then extracted 3 times with ethyl acetate. The combined ethyl acetate phases are washed with water, dried and concentrated. The crude product is dissolved in a small amount of CHCl3—CH3OH—95:5 and chromatographed on 100 g of silica gel. The column is eluted with chloroform which contains increasing proportions of methanol (5 to 100%). The fractions containing the desired product as determined by thin-layer chromatography are combined. Precipitation from acetone/ether/hexane yields Papulacandin B-12-(carboxymethyl) ether as a colourless amorphous powder.

Rf-value: 0.29 in CHCl3—CH2OH-1:1, 0.36 in n-butanol-CH3COOH-H2O-11:3:7.

UV: $\lambda_{max}$ ($\epsilon$) (ethanol): 235 (33 200), 265 (34 200), 297 (24 000).

IR: (in KBr): 3500,2970,1710,1615,1430,1265,1150,1065,1035 cm$^{-1}$.

13C-NMR: 68.54 ppm (O—<u>C</u>H2—COOH), 156.18 ppm (C-12), 162.13 ppm (C-10), 177.01 ppm (—CH2—<u>C</u>OOH).

2.4 g of Papulacandin B-10,12-di-(p-nitrobenzyloxycarbonylmethyl) ether are dissolved in 160 ml of acetic acid and 80 ml of methanol. Then 4.8 g of zinc dust are added to the solution and the mixture is stirred intensively for 30 minutes at room temperature. The reaction solution is filtered over Celite and subsequently evaporated to dryness under mild conditions. The residue is dissolved in a small amount of methanol and chromatographed on 150 g of Sephadex-LH-20. The column is eluted with methanol. The fractions containing the desired product as determined by thin-layer chromatography are combined. Precipitation from methanol/ether/hexane yields Papulacandin B-10,12-di-(carboxymethyl)ether as a colourless amorphous powder.

Rf-value: 0.14 in n-butanol—CH3COOH—H2O—11:3:7

UV: $\lambda$max ($\epsilon$) (ethanol): 235 nm (32 300), 265 nm (32 500), 295 nm (22 200).

IR: (in KBr): 3500,2970,1710,1615,1495,1420,1300,1205,1150,1065 cm$^{-1}$.

| 13C—NMR: | 156.01 ppm | (C-12) |
|---|---|---|
| | 163.62 ppm | (C-10) |
| | 176.64 ppm | (2x-OCH2—<u>C</u>OOH) |
| | 176.88 ppm | |

EXAMPLE 7

1.5 g of Papulacandin B, 3.9 g of silver oxide (10 equivalents) and 3 g of benzyl bromide (10 equivalents) are intensively stirred in 150 ml of dimethyl formamide for 1¾ hours at room temperature until Papulacandin B can no longer be detected by thin-layer chromatography. The reaction solution is filtered over Celite and thereafter evaporated to dryness in vacuo. The residue is dissolved in methanol, filtered once more over Celite and evaporated to dryness. The crude product is subsequently dissolved in chloroform and chromatographed on 120 g of silica gel. The column is eluted with chloroform containing increasing proportions of methanol (2–20%). The fractions containing the desired product as determined by thin-layer chromatography are combined. Precipitation from acetone/ether/hexane yields Papulacandin B-10,12-dibenzyl ether and Papulacandin B-12-monobenzyl ether as a colourless amorphous powder.

Papulacandin B-12-mono-benzyl ether

Rf-value: B 0.36 in CHCl3—CH3OH—(4:1)

UV: $\lambda_{max}$. ($\epsilon$) (ethanol): 234 nm (16 400), 265 nm (16 600), 298 nm (11 200).

IR (in KBr): 3500,2960,1705,1615,1455,1380,1345,1310,1205,1155,1070 cm$^{-1}$.

| 13C—NMR: | 69.66 ppm | (OCH2—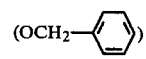) |
|---|---|---|
| | 129.50 ppm | |
| | 130.33 ppm | (additional aromatic C-atoms) |
| | 134.31 ppm | |
| | 156.42 ppm | (C-12) |

| | |
|---|---|
| 161.90 ppm | (C-10) |

1H-NMR: 7.3 bis 7.6 ppm (aromatic protons).
Papulacandin B-10,12-di-benzyl ether
Rf-value: 0.52 in CHCl3—CH3OH—(4:1)
UV: λ$_{max}$ (ε) (ethanol): 230 nm (37 600), 265 nm (35 200), 295 nm shoulder.
IR: (in KBr): 3500,2970,1710,1615,1500,1460,1380,1345,1305,1265,1155,1070,1010 cm$^{-1}$.

| 13C—NMR: | 128.19 ppm | |
|---|---|---|
| | 128.50 ppm | |
| | 128.88 ppm | (additional aromatic C-atoms) |
| | 129.51 ppm | |
| | 138.36 ppm | |
| | 156.30 ppm | (C-12) |
| | 163.36 ppm | (C-10) |

1H-NMR: 7.2 bis 7.7 ppm (aromatic protons).

EXAMPLE 8

20 g of Papulacandin B, 25.8 g of silver oxide (5 equivalents) and 19.2 g of p-nitrobenzyl bromide (4 equivalents) are intensively stirred in 1500 ml of dimethyl formamide for 2¾ hours at room temperature until Papulacandin B can no longer be detected by thin-layer chromatography. The reaction solution is filtered over Celite and thereafter evaporated to dryness in vacuo. The residue is dissolved in methanol, filtered once more over Celite and evaporated to dryness. The crude product is subsequently dissolved in chloroform and chromatographed on a column of 100 g of silica gel. The column is eluted with chloroform containing increasing proportions of methanol (2–20%). The fractions containing the desired product as determined by thin-layer chromatography are combined. Precipitation from acetone/ether/hexane yields Papulacandin B-10,12-di-p-nitrobenzyl ether and Papulacandin B-12-p-nitrobenzyl ether as a colourless amorphous powder.

Papulacandin B-12-mono-p-nitrobenzyl ether
Rf-value: 0.48 in CHCl3—CH3OH—(4:1)
UV: λ$_{max}$ (ε) (ethanol): 238 nm (42 400), 267 nm (50 200), 298 nm, shoulder.
IR: (in KBr): 3500,2900,1715,1625,1535,1355,1265,1160,1065 cm$^{-1}$.

1H-NMR: 7.75 to 8.20 (aromatic protons of the p-nitrobenzyl group).

| 13C—NMR: | 69.80 ppm | O—CH$_2$—C$_6$H$_4$—NO$_2$ |
|---|---|---|
| | 124.62 ppm | |
| | 128.79 ppm | signals of the aromatic C-atoms of |
| | 146.24 ppm | the p-nitrobenzyl group |
| | 148.68 ppm | |
| | 155.83 ppm | (C-12) |
| | 161.90 ppm | (C-10) |

Papulacandin B-10,12-di-p-nitrobenzyl ether
Rf-value: 0.67 in CHCl3—CH3OH—(4:1)
UV: λ$_{max}$ (ε) (ethanol): 240 nm (49 200), 267 nm (66 000), 298 nm shoulder.
IR: (in KBr): 3500,2970,1710,1615,1525,1350,1265,1160 cm$^{-1}$.

1H-NMR: 7.6 to 8.2 ppm (aromatic protons of the p-nitrobenzyl group).

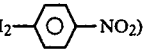

| 13C—NMR: | 70.21 ppm | (2 × O—CH$_2$—C$_6$H$_4$—NO$_2$) |
|---|---|---|
| | 124.66 ppm | |
| | 129.06 ppm | signals of the aromatic C-atoms of |
| | 146.04 ppm | the p-nitrobenzyl group |
| | 149.19 ppm | |
| | 156.14 ppm | (C-12) |
| | 163.19 ppm | |

EXAMPLE 9

5 g of Papulacandin B-12-p-nitrobenzyl ether, 11.2 g of silver oxide (10 equivalents) and 36.4 g of p-nitrobenzyl bromoacetate (25 equivalents) are intensively stirred in 500 ml of dimethyl formamide for 1¾ hours at room temperature until all the starting material can no longer be detected by thin-layer chromatography. The reaction solution is filtered over Celite and thereafter evaporated to dryness in vacuo. The residue is dissolved in methanol, filtered once more over Celite and evaporated to dryness. The crude product is subsequently dissolved in chloroform and chromatographed on 130 g of silica gel. The column is eluted with chlorofrom containing increasing proportions of methanol (2–20%). The fractions containing the desired product as determined by thin-layer chromatography are combined. Precipitation from acetone/ether/hexane yields Papulacandin B-12-p-nitrobenzyl-10-(p-nitrobenzyloxycarbonylmethyl)ether as a colourless amorphous powder.

Removal of the p-nitrobenzyl groups 1.7 g of Papulacandin B-12-p-nitrobenzyl-10-(p-nitrobenzyloxycarbonylmethyl)ether are dissolved in 100 ml of acetic acid and 40 ml of methanol. Then 3.4 g of zinc dust are added to the solution and the mixture is intensively stirred for 15 minutes at 0° C. The reaction solution is filtered over Celite and subsequently evaporated to dryness under mild conditions. The residue is dissolved in methanol and the solution is diluted with water and then extracted 3 times with ethyl acetate. The combined ethyl acetate phases are washed once with water, dried and evaporated to dryness. The crude product is subsequently dissolved in a small amount of methanol and chromatographed on Sephadex-LH-20. The column is eluted with methanol. The fractions containing the desired product as determined by thin-layer chromatography are combined. Precipitation from acetone/ether/hexane yields Papulacandin B-10-(carboxymethyl)ether.

Rf-value: 0.50 in n-butanol/glacial acetic acid/water (11:3:7)
UV: λ$_{max}$ (ε) (ethanol): 238 (37 000), 265 (38 400), 298 (28 200).
IR (in KBr): 3500,2970,1705,1615,1455,1305,1265,1155 cm$^{-1}$.
13C-NMR: 154.54 ppm (C-12), 162.83 ppm (C-10).

Sodium salt 360 mg of Papulacandin B-10-(carboxymethyl)ether are dissolved in dioxane and the solution is treated with 1 equivalent of 0.1 N sodium hydroxide solution and lyophilised to give the sodium salt as a colourless powder.

EXAMPLE 10

2.59 g of Papulacandin B-12-p-nitrobenzyl ether, 5.8 g of silver oxide (10 equivalents) and 3.83 g of methyl bromoacetate (10 equivalents) are intensively stirred in 200 ml of dimethyl formamide for 3 hours at room temperature until all the starting material can no longer be detected by thin-layer chromatography. The reaction solution is filtered over Celite and thereafter evaporated to dryness in vacuo. The residue is dissolved in methanol, filtered once more over Celite and evaporated to dryness. The crude product is subsequently dissolved in chloroform and chromatographed on 100 g of silica gel. The column is eluted with chloroform containing increasing proportions of methanol (2–20%). The fractions containing the desired product as determined by thin-layer chromatography are combined. Precipitation from acetone/ether/hexane yields Papulacandin B-12-p-nitrobenzyl-10-(methoxycarbonylmethyl)ether as a colourless amorphous powder.

Removal of the p-nitrobenzyl group 1.47 g of Papulacandin B-12-p-nitrobenzyl-10-(methoxycarbonylmethyl)ether are dissolved in 70 ml of acetic acid and 30 ml of methanol. Then 3 g of zinc dust are added to the solution and the mixture is stirred intensively for 12 minutes at 0° C. The reaction solution is filtered over Celite and subsequently evaporated to dryness under mild conditions. The residue is dissolved in a small amount of methanol and the solution is diluted with water and then extracted 3 times with ethyl acetate. The combined ethyl acetate phases are washed with water, dried and concentrated. The crude product is dissolved in a small amount of $CHCl_3$—$CH_3OH$—98:2 and chromatographed on 100 g of silica gel. The column is eluted with chloroform containing increasing proportions of methanol (2 to 20%). The fractions containing the desired product as determined by thin-layer chromatography are combined. Precipitation from acetone/ether/hexane yields Papulacandin B-10-(methoxycarbonylmethyl)ether as a colourless amorphous powder.

Rf-value: 0.36 in $CHCl_3$—$CH_3OH$—4:1

UV: $\lambda_{max}$ ($\epsilon$) (ethanol) 240 (39 000), 260 (41 200), 296 (shoulder).

IR (in KBr): 3500,2950,1745 (shoulder), 1710,1615,1455,1385,1340,1315,1265,1150 $cm^{-1}$.

$^{13}$C-NMR: 52.62 ppm (—COO$\underline{C}H_3$), 66.14 ppm (O—$\underline{C}H_2$COOCH$_3$), 154.44 ppm (C-10), 162.10 ppm (C-12).

The following compounds are prepared in analogous manner:

(1) Papulacandin B-10-(ethoxycarbonylmethyl)ether
(2) Papulacandin B-10-(2-hydroxyethoxycarbonylmethyl)ether
(3) Papulacandin B-10-(2,3-dihydroxypropyloxycarbonylmethyl)ether.

EXAMPLE 11

2 g of Papulacandin B-12-p-nitrobenzyl ether, 9.2 g of silver oxide (2 equivalents) and 9 g of iodoacetamide (25 equivalents) are intensively stirred in 300 ml of dimethyl formamide for 6 hours at room temperature until all the starting material can no longer be detected by thin-layer chromatography. The reaction solution is filtered over Celite and thereafter evaporated to dryness in vacuo. The residue is dissolved in methanol, filtered once more over Celite and evaporated to dryness. The crude product is subsequently dissolved in chloroform and chromatographed on 100 g of silica gel. The column is eluted with chloroform containing increasing proportions of methanol (2–20%). The fractions containing the desired product as determined by thin-layer chromatography are combined. Precipitation from acetone/ether/hexane yields Papulacandin B-12-p-nitrobenzyl-10-(carbamoylmethyl)ether as a colourless amorphous powder.

Removal of the p-nitrobenzyl group 1.27 g of Papulacandin B-12-p-nitrobenzyl-10-(carbamolymethyl) ether are dissolved in 130 ml of acetic acid and 70 ml of methanol. The 2.5 g of zinc dust are added to the solution and the mixture is stirred intensively for 12 minutes at 0° C. The reaction solution is filtered over Celite and subsequently evaporated to dryness under mild conditions. The residue is dissolved in a small amount of methanol and the solution is diluted with water and then extracted 3 times with ethyl acetate. The combined ethyl acetate phases are washed with water, dried and concentrated. The crude product is dissolved in a small amount of $CHCl_3$—$CH_3OH$—98:2 and chromatographed on 100 g of silica gel. The column is eluted with chloroform containing increasing proportions of methanol (2 to 20%). The fractions containing the desired product as determined by thin-layer chromatography are combined. Precipitation from acetone/ether/hexane yields Papulacandin B-10-(carbamoylmethyl)ether as a colourless amorphous powder.

Rf-value: 0.21 in $CHCl_3$—$CH_3OH$—4:1

UV: $\lambda_{max}$ ($\epsilon$) (ethanol): 231 (37 400), 239 (37 600), 266 (41 000), 297 (29 400).

IR (in KBr): 3500,2970,1700,1645,1620,1515,1460,1305,1265,1150,1070,1035,1010 $cm^{-1}$.

$^{13}$C-NMR: 68.24 ppm (O—$\underline{C}H_2$—CO—NH$_2$), 154.71 ppm (C-12), 162.07 ppm (C-10), 173.88 ppm (—$\underline{C}O$—NH$_2$).

EXAMPLE 12

2 g of Papulacandin B-12-p-nitrobenzyl ether, 4.5 g of silver oxide (10 equivalents) and 8 g of α-bromo-N-(dimethylacetamide) (25 equivalents) are intensively stirred in 200 ml of dimethyl formamide for 30 minutes at room temperature until all the starting material can no longer be detected by thin-layer chromatography. The reaction solution is filtered over Celite and thereafter evaporated to dryness in vacuo. The residue is taken up in methanol, filtered once more over Celite and evaporated to dryness. The crude product is subsequently dissolved in chloroform and chromatographed on 200 g of silica gel. The column is eluted with chloroform containing increasing proportions of methanol (2–20%). The fractions containing the desired product as determined by thin-layer chromatography are combined. Precipitation from acetone/ether/hexane yields Papulacandin B-12-p-nitrobenzyl-10-(N-dimethylcarbamoylmethyl)ether as a colourless amorphous powder.

Removal of the p-nitrobenzyl group 1 g of Papulacandin B-12-p-nitrobenzyl-10-(N-dimethylcarbamoylmethyl)ether are dissolved in 100 ml of acetic acid and 40 ml of methanol. Then 2 g of zinc dust are added to the solution and the mixture is stirred intensively for 12 minutes at 0° C. The reaction solution is filtered over Celite and subsequently evaporated to dryness under mild conditions. The residue is dissolved in a small amount of methanol and the solution is diluted with water and then extracted 3 times with ethyl acetate. The combined ethyl acetate phases are washed with water, dried and concentrated. The crude product is dissolved in a small amount of CHCl₃—CH₃OH—98:2 and chromatographed on 100 g of silica gel. The column is eluted with chloroform containing increasing proportions of methanol (2 to 20%). The fractions containing the desired product as determined by thin-layer chromatography are combined. Precipitation from acetone/ether/hexane yields Papulacandin B-10-(N-dimethylcarbamoylmethyl)ether as a colourless amorphous powder. The following compounds are obtained in analogous manner:

(1) Papulacandin B-10-(N-methylcarbamoylmethyl)ether
(2) Papulacandin B-10-(N-ethylcarbamoylmethyl)ether
(3) Papulacandin B-10-(N-diethylcarbamoylmethyl)ether
(4) Papulacandin B-10-(N-hydroxyethylcarbamoylmethyl)ether

EXAMPLE 13

1 g of Papulacandin B-12-p-nitrobenzyl ether, 2.39 g of silver oxide (10 equivalents) and 1.41 g of bromoacetone (10 equivalents) are intensively stirred in 200 ml of dimethyl formamide for 4 hours at 0° C. until all the starting material can no longer be detected by thin-layer chromatography. The reaction solution is filtered over Celite and thereafter evaporated to dryness in vacuo. The residue is taken up in methanol, filtered once more over Celite and evaporated to dryness. The crude product is subsequently dissolved in chloroform and chromatographed on a column of 100 g of silica gel. The column is eluted with chloroform containing increasing proportions of methanol (2–20%). The fractions containing the desired product as determined by thin-layer chromatography are combined. Precipitation from acetone/ether/hexane yields Papulacandin B-12-p-nitrobenzyl-10-(2'-oxopropyl)ether as a colourless amorphous powder.

Removal of the p-nitrobenzyl group 600 mg of Papulacandin B-12-p-nitrobenzyl-10-(2'-oxopropyl)ether are dissolved in 60 ml of acetic acid and 25 ml of methanol. The 1.2 g of zinc dust are added to the solution and the mixture is stirred intensively for 12 minutes at 0° C. The reaction solution is filtered over Celite and subsequently evaporated to dryness under mild conditions. The residue is dissolved in a small amount of methanol and the solution is diluted with water and then extracted 3 times with ethyl acetate. The combined ethyl acetate phases are washed with water, dried and concentrated. The crude product is dissolved in a small amount of CHCl₃—CH₃OH—98:2 and chromatographed on 50 g of silica gel. The column is eluted with chloroform containing increasing proportions of methanol (2 to 20%). The fractions containing the desired product as determined by thin-layer chromatography are combined. Precipitation from acetone/ether/hexane yields Papulacandin B-10-(2'-oxopropyl) ether as a colourless amorphous powder.

Rf-value: 0.37 in CHCl₃—CH₃OH—4:1

UV: $\lambda_{max.}$ ($\epsilon$) (ethanol): 232 nm (35 800), 267 nm (36 000), 298 nm (shoulder).

IR: (in KBr): 3500, 2950, 1710, 1020, 1465, 1430, 1350, 1265, 1155, 1065 cm⁻¹.

¹³C-NMR: 26.34 ppm (—OCH₂CO—CH₃), 154.52 ppm (C-12), 162.17 ppm (C-10), 206.93 ppm (—OCH₂CO—CH₃).

EXAMPLE 14

1.03 g of Papulacandin B-12-p-nitrobenzyl ether, 2.35 g of silver oxide (10 equivalents) and 6.15 g of (bromoacetyl)thiophene (30 equivalents) are intensively stirred in 300 ml of dimethyl formamide for 2 hours at room temperature until all the starting material can no longer be detected by thin-layer chromatography. The reaction solution is filtered over Celite and thereafter evaporated to dryness in vacuo. The residue is taken up in methanol, filtered once more over Celite and evaporated to dryness. The crude product is subsequently dissolved in chloroform and chromatographed on a column of 110 g of silica gel. The column is eluted with chloroform containing increasing proportions of methanol (2–20%). The fractions containing the desired product as determined by thin-layer chromatography are combined. Precipitation from acetone/ether/hexane yields Papulacandin B-12-p-nitrobenzyl-10-(2-thienylcarbonylmethyl) ether as a colourless amorphous powder.

Removal of the p-nitrobenzyl group 500 mg of Papulacandin B-12-p-nitrobenzyl-10-(2-thienylcarbonylmethyl) ether are dissolved in 50 ml of acetic acid and 15 ml of methanol. Then 1 g of zinc dust is added to the solution and the mixture is stirred intensively for 12 minutes at 0° C. The reaction solution is filtered over Celite and subsequently evaporated to dryness under mild conditions. The residue is dissolved in a small amount of methanol and the solution is diluted with water and then extracted 3 times with ethyl acetate. The combined ethyl acetate phases are washed with water, dried and concentrated. The crude product is dissolved in a small amount of CHCl₃—CH₃OH—98:2 and chromatographed on 70 g of silica gel. The column is eluted with chloroform containing increasing proportions of methanol (2 to 20%). The fractions containing the desired product as determined by thin-layer chromatography are combined. Precipitation from acetone/ether/hexane yields Papulacandin B-10-(2-thienylcarbonylmethyl) ether as a colourless amorphous powder.

Rf-value: 0.46 in CHCl₃—CH₃OH—4:1

UV: $\lambda_{max}$ ($\epsilon$) (ethanol): 235 (shoulder), 242 (38 600), 262 (45 600).

IR: (in KBr) 3500, 2970, 1710, 1645, 1615, 1510, 1455, 1420, 1385, 1265, 1170 cm⁻¹.

¹³C—NMR: 129.70 ppm ⎫
134.70 ppm ⎪
136.05 ppm ⎬ additional olefinic C-atoms
140.97 ppm ⎭
154.49 ppm   (C-12)
162.24 ppm   (C-10)
189.87 ppm   (OCH₂CO—)

EXAMPLE 15

30 g of Papulacandin A, 50 g of silver oxide (8 equivalents) and 30 g of p-nitrobenzyl bromide (4 equivalents) are intensively stirred in 1000 ml of dimethyl formamide for 5 hours at room temperature until all the starting material can no longer be detected by thin-layer chromatography. The reaction solution is filtered over Celite and thereafter evaporated to dryness in vacuo. The residue is taken up in methanol, filtered once more over Celite and evaporated to dryness. The crude product is subsequently dissolved in chloroform and chromatographed on a column of 1 kg of silica gel. The column is eluted with chloroform containing increasing proportions of methanol (2–20%). The fractions containing the desired product as determined by thin-layer chromatography are combined. Precipitation from acetone/ether/hexane yields Papulacandin A-di-10,12-p-nitrobenzyl ether and Papulacandin A-12-p-nitrobenzyl ether as colourless amorphous powders.

Papulacandin A-12-p-nitrobenzyl ether
Rf-value: 0.43 in CHCl$_3$—CH$_3$OH—4:1
UV: $\lambda_{max}$. ($\epsilon$) (ethanol) 235 (shoulder), 263 (37 500).
IR (in KBr): 3500, 2970, 1710, 1610, 1525, 1350, 1245, 1155 cm$^{-1}$.

| $^{13}$C—NMR: | 69.72 ppm | |
|---|---|---|
| | | (OCH$_2$—⟨O⟩—NO$_2$) |
| | 124.62 ppm | |
| | 128.94 ppm ⎫ | signals of the aromatic C-atoms |
| | 146.24 ppm ⎬ | of the p-nitrobenzyl group |
| | 148.77 ppm ⎭ | |
| | 155.89 ppm | (C-12) |
| | 161.99 ppm | (C-10) |

EXAMPLE 16

3.75 g of Papulacandin A-12-p-nitrobenzyl ether, 7.4 g of silver oxide (10 equivalents) and 11 g of p-nitrobenzyl bromoacetate (10 equivalents) are intensively stirred in 300 ml of dimethyl formamide for 4 hours at 0° C. until all the starting material can no longer be detected by thin-layer chromatography. The reaction solution is filtered over Celite and thereafter evaporated to dryness in vacuo. The residue is taken up in methanol, filtered once more over Celite and evaporated to dryness. The crude product is subsequently dissolved in chloroform and chromatographed on a column of 200 g of silica gel. The column is eluted with chloroform containing increasing proportions of methanol (2–20%). The fractions containing the desired product as determined by thin-layer chromatography are combined. Precipitation from acetone/ether/hexane yields Papulacandin A-12-p-nitrobenzyl-10-(p-nitrobenzyloxycarbonylmethyl) ether as a colourless amorphous powder.

Removal of the p-nitrobenzyl groups 1.4 g of Papulacandin A-12-p-nitrobenzyl-10-(p-nitrobenzyloxycarbonylmethyl) ether are dissolved in 140 ml of acetic acid and 60 ml of methanol. Then 2.8 g of zinc dust are added to the solution and the mixture is stirred intensively for 12 minutes at 10° C. The reaction solution is filtered over Celite and subsequently evaporated to dryness under mild conditions. The residue is dissolved in a small amount of methanol and the solution is diluted with water and then extracted 3 times with ethyl acetate. The combined ethyl acetate phases are washed with water, dried and concentrated. The crude product is dissolved in a small amount of CHCl$_3$—CH$_3$OH—98:2 and chromatographed on 120 g of silica gel. The column is eluted with chloroform containing increasing proportions of methanol (2 to 20%). The fractions containing the desired product as determined by thin-layer chromatography are combined. Precipitation from acetone/ether/hexane yields Papulacandin A-10-carboxymethyl ether as a colourless amorphous powder.

Rf value: 0.5 in n-butanol/glacial acetic acid/water (11:3:7)

UV: $\lambda_{max}$ ($\epsilon$) (ethanol): 242 (42 000), 264 (49 700).

IR: (in KBr): 3500, 2970, 1705, 1640, 1615, 1455, 1265, 1160, 1075, 1035 cm$^{-1}$.

$^{13}$C-NMR: 154.29 ppm (C-12), 162.49 ppm (C-10).

Sodium salt 300 mg of Papulacandin A-10-carboxymethyl ether are dissolved in dioxane, treated with 1 equivalent of 0.1 N sodium hydroxide and lyophilised, to give the sodium salt as a colourless powder.

EXAMPLE 17

Pharmaceutical preparation in the form of a gel for treating viral infections and containing Papulacandin B-10-carboxymethyl ether.

Gel with a content of 0.05% of active substance

To prepare 5 liters of gel, 100 g of highly viscous methyl cellulose are mixed with 500 g of propylene glycol and 3.25 ml of aqua conservans and the mixture is allowed to swell to a homogeneous mucilage. Then a suspension of 2.5 g of Papulacandin B-10-carboxymethyl ether in 1 liter of aqua conservans is added. Finally, aqua conservans is added in an amount sufficient to make up 5 liters, the batch is carefully mixed and the resultant gel is packed into tubes. By aqua conservans is meant an aqueous solution of 0.07% of methyl p-hydroxybenzoate (methyl parabene) and 0.03% of propyl p-hydroxybenzoate (propyl parabene).

EXAMPLE 18

Pharmaceutical preparation for treating fungus infections containing Papulacandin B-10-methoxycarbonylmethyl ether Gels containing between 0.5 and 1% of the active substance are prepared as in Example 17 using the respective necessary amounts of Papulacandin B 10-methoxycarbonylmethyl ether.

What is claimed is:

1. A member selected from the group consisting of mono- and diethers of Papulacandin A of the formula and mono- and diethers of Papulacandin B of the formula

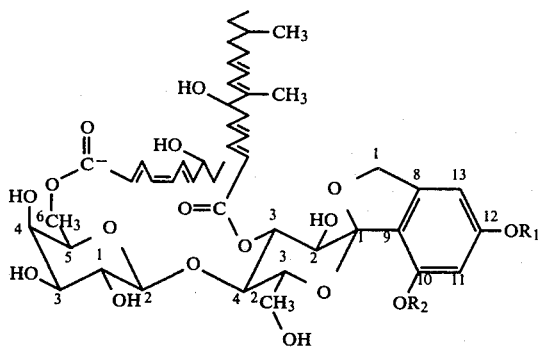

wherein each of $R_1$ and $R_2$ represents hydrogen or an unsubstituted or substituted hydrocarbon radical of the formula (IV) —$CH_2$—K having not more than 24 C atoms wherein K represents a member selected from the group consisting of
(1) an unsubstituted unsaturated aliphatic hydrocarbon radical having 1–7 C atoms,
(2) a member selected from the group consisting of phenyl, cycloalkyl of 3–8 ring C atoms, cycloalkenyl of 3–8 ring C atoms, cycloalkadienyl of 3–8 ring C atoms, and derivatives of these 4 groups substituted by alkyl groups having 1–4 C atoms
or
(3) a monocyclic heterocyclic radical selected from the group consisting of a 6-membered mono-aza-cyclic radical, a 5-membered mono-thia-cyclic radical and a 5-membered mono-oxa-cyclic radical, and derivatives of any of these heterocyclic radicals substituted at the ring by alkyl groups having 1–4 C atoms
or
(4) a saturated or unsaturated aliphatic hydrocarbon radical of 1–7 C atoms substituted by a member selected from the group consisting of phenyl, cycloalkyl of 3–8 ring C atoms, cycloalkenyl of 3–8 ring C atoms, cycloalkadienyl of 3–8 ring C atoms, a 6-membered mono-aza-cyclic radical, a 5-membered mono-thia-cyclic radical and a 5-membered mono-oxa-cyclic radical, and a derivative of any of these cyclic groups substituted at the ring by alkyl groups having 1–4 C atoms, or a saturated or unsaturated aliphatic hydrocarbon radical of 1–7 C atoms interrupted in the —C—C-chain by a divalent radical corresponding to any of the cyclic substituents mentioned, or K represents any radical as defined under items (1) to (4) which are furthermore substituted by one or more functional groups selected from the group consisting of free, etherified and esterified hydroxyl groups, mercapto, alkylthio and phenylthio groups, halogen atoms, cyano, azido, oxo and nitro groups, primary and secondary amino groups and corresponding acylamino groups, sulphamino groups, free carboxyl groups or esterified carboxyl groups, carbamoyl, ureidocarbonyl, guanidinocarbonyl or groups derived therefrom by substitution of the hydrogens of the $NH_2$ group by lower alkyl, hydroxyalkyl or alkoxyalkyl groups, and sulpho groups, the acyl groups of esterified hydroxyl groups being derived from a carboxylic or sulphonic acid having not more than 18 C-atoms, and the ether groups or esterified carboxylic acid groups being derived from lower aliphatic alcohols, benzyl alcohol or benzhydrol or nitro or amino derivatives thereof, 2-tetrahydrofuranol or 2-tetrahydropyranol, tri-lower-alkylsilyl alcohol and phenyl-di-lower alkylsilyl-alcohol, with the proviso that at least one of the symbols $R_1$ and $R_2$ represents the hydrocarbon of the formula (IV),
and therapeutically useful metal salts of the acidic ethers as defined and therapeutically useful acid addition salts or quaternary ammonium salts of the basic ethers as defined.

2. A compound according to claim 1, wherein $R_1$ or $R_2$ in formula (III) are hydrogen or a radical of one of the partial formulae

—$CH_2$—$A_1$

—$CH_2$—$Kw_1$—$A_1$

—$CH_2$—$Kw_2$—$A_2$—$Kw_3$ in which $Kw_1$ represents a saturated or unsaturated linear or branched aliphatic hydrocarbon radical containing 1 to 7 carbon atoms, and each of $Kw_2$ and $Kw_3$ also represents such a radical, with the proviso that $Kw_2$ and $Kw_3$ together do not contain more than 7 C atoms, and $A_1$ represents a monocyclic hydrocarbon radical or a monocyclic heterocyclic radical and $A_2$ represents a monocyclic hydrocarbon radical or a monocyclic heterocyclic radical, with the proviso that at least one of $R_1$ and $R_2$ is one of the said radicals.

3. A 10-mono-ether of Papulacandin B according to claim 1, wherein K in formula (IV) is a member selected from the group consisting of
(a) a free carboxyl group, an esterified carboxyl group, a carbamide group which is N-unsubstituted or N-substituted by one or two lower alkyl radicals of 1 to 7 carbon atoms, a cyano group
(b) a lower alkyl radical of 1 to 7 carbon atoms which is substituted by any of the groups mentioned in (a), any ester group being derived from a lower mono- or polyhydric alcohol of 1 to 7 carbon atoms, and lower alkyl radicals substituting the amide N being optionally substituted by hydroxy or amino.

4. A 12-monoether of Papulacandin A or Papulacandin B according to claim 1.

5. A 10,12-diether of Papulacandin A or Papulacandin B according to claim 1.

6. A 10-monoether of Papulacandin A or Papulacandin B according to claim 1.

7. A compound according to claim 1 wherein the ether groups contain functional groups which are capable of salt formation, and the water-soluble salts thereof.

8. Acid addition salts of a compound according to claim 1 which contain basic groups which are derived from therapeutically useful acids.

9. Quaternary ammonium salts of a compound according to claim 1 which are derived from therapeutically useful acids.

10. A diether of Papulacandin A and B according to claim 1 wherein the ether radical in the 12-position is p-nitrobenzyl or p-aminobenzyl.

11. A compound as claimed in claim 1 which is a member selected from the group consisting of Papulacandin B-10,12-diallyl ether and Papulacandin B-12- monoallyl ether, Papulacandin B-10,12-di-(3-iodopropyl) ether and Papulacandin 12-mono-(3-iodopropyl) ether, Papulacandin B-10,12-di-(2-oxo-propyl) ether and Papulacandin B-12-mono-(2-oxo-propyl) ether, Papulacandin B-10,12-di-(methoxycarbonylmethyl) ether and Papulacandin B-12-mono-(methoxycarbonylmethyl) ether, Papulacandin B-10,12-dibenzylether and Papulacandin B-12-mono-benzyl ether, Papulacandin B-di-(p-nitrobenzyloxycarbonylmethyl) ether and Papulacandin B-12-mono-(p-nitrobenzyloxycarbonylmethyl) ether, Papulacandin B-12-mono-(carboxymethyl) ether and Papulacandin B-10,12-di-(carboxymethyl) ether, and Papulacandin B-12-mono-p-nitrobenzylether and Papulacandin-B-10,12-di-p-nitrobenzyl ether.

12. A claim as claimed in claim 1 which is a member selected from the group consisting of Papulacandin B-10-carboxylmethyl ether, Papulacandin B-10-(methoxycarbonylmethyl) ether, Papulacandin B-10-(ethoxycarbonyl-methyl) ether, Papulacandin 10-(2-hydroxyethoxycarbonylmethyl) ether, Papulacandin B-10-(2,3-dihydroxypropyloxycarbonylmethyl) ether, Papulacandin B-10-(carbamoylmethyl) ether, Papulacandin B-10-(N-mono- or dialkylcarbamoylmethyl) ether, wherein alkyl is methyl or ethyl, Papulacandin B-10-(N-hydroxyethylcarbamoylmethyl) ether, Papulacandin B-10-(2-oxopropyl) ether, Papulacandin B-10(2-thienylcarbonylmethyl) ether, Papulacandin A-10,12-di-(p-nitrobenzyl) ether and Papulacandin A-12-Mono-p-nitrobenzyl ether, and Papulacandin A-10-carboxymethyl ether.

13. A pharmaceutical preparation which contains a compound as claimed in claim 1 together with a suitable pharmaceutical carrier.

* * * * *